US012636205B2

(12) United States Patent
Lindner et al.

(10) Patent No.: US 12,636,205 B2
(45) Date of Patent: May 26, 2026

(54) ABSORBENT CORES COMPRISING A SUPERABSORBENT POLYMER IMMOBILIZING MATERIAL

(71) Applicant: The Procter & Gamble Company, Cincinnati, OH (US)

(72) Inventors: Torsten Lindner, Kronberg (DE); Robert Haines Turner, Cincinnati, OH (US); Christian Neu, Eppstein (DE); Matthias Morand, Sulzbach (DE); Gabriele Stiehl, Bad Soden (DE); Erik Hauck, Pirmasens (DE); Jeremia Schwabe, Augsburg (DE); Simon Bodendorfer, Gersthofen (DE); Matthias Roessle, Reutern (DE); Sebastijan Bach, Charloette, NC (US)

(73) Assignee: The Procter & Gamble Company, Cincinnati, OH (US)

( * ) Notice: Subject to any disclaimer, the term of this patent is extended or adjusted under 35 U.S.C. 154(b) by 166 days.

(21) Appl. No.: 18/457,526

(22) Filed: Aug. 29, 2023

(65) Prior Publication Data

US 2024/0000636 A1 Jan. 4, 2024

Related U.S. Application Data

(63) Continuation of application No. 16/520,386, filed on Jul. 24, 2019, now Pat. No. 11,779,496.
(Continued)

(51) Int. Cl.
*A61F 13/15* (2006.01)
*A61F 13/45* (2006.01)
(Continued)

(52) U.S. Cl.
CPC ............ *A61F 13/534* (2013.01); *A61F 13/45* (2013.01); *B01J 20/264* (2013.01);
(Continued)

(58) Field of Classification Search
CPC .................... A61F 13/534; A61F 13/45; A61F 2013/15463; A61F 2013/4587;
(Continued)

(56) References Cited

U.S. PATENT DOCUMENTS

| 3,860,003 A | 1/1975 | Buell |
| 3,911,173 A | 10/1975 | Sprague, Jr. |

(Continued)

FOREIGN PATENT DOCUMENTS

| EP | 0149880 A2 | 7/1985 |
| EP | 3085346 A1 | 10/2016 |
| WO | 9516746 A1 | 6/1995 |

OTHER PUBLICATIONS

All Office Actions; U.S. Appl. No. 16/520,386.
International Search Report and Written Opinion; Application Ser. No. PCT/US2019/043133; dated Oct. 24, 2019, 10 pages.

*Primary Examiner* — Jacqueline F Stephens
(74) *Attorney, Agent, or Firm* — Anna E. Haller; Amanda Herman Berghauer

(57) ABSTRACT

Described herein is an absorbent article having an absorbent core. The absorbent core includes a superabsorbent polymer material and an auxiliary adhesive. The auxiliary adhesive includes from about 20% to about 70% of a first polymer and from about 30% to about 80% of a second polymer. The auxiliary adhesive has a Shear Viscosity at 10 (1/s) at 230° C. of from about 300 mPa·s to about mPa·s.

20 Claims, 13 Drawing Sheets

Related U.S. Application Data

(60) Provisional application No. 62/703,585, filed on Jul. 26, 2018.

(51) Int. Cl.

| | |
|---|---|
| *A61F 13/534* | (2006.01) |
| *B01J 20/26* | (2006.01) |
| *A61F 13/53* | (2006.01) |

(52) U.S. Cl.
CPC .............. *A61F 2013/15463* (2013.01); *A61F 2013/4587* (2013.01); *A61F 2013/530481* (2013.01); *A61F 2013/53463* (2013.01); *B01J 2220/68* (2013.01)

(58) Field of Classification Search
CPC ......... A61F 2013/530481; A61F 2013/53463; B01J 20/264; B01J 2220/68
See application file for complete search history.

(56) References Cited

U.S. PATENT DOCUMENTS

| | | |
|---|---|---|
| 3,929,135 A | 12/1975 | Thompson |
| 4,100,324 A | 7/1978 | Anderson |
| 4,324,246 A | 4/1982 | Mullane et al. |
| 4,342,314 A | 8/1982 | Radel et al. |
| 4,463,045 A | 7/1984 | Ahr et al. |
| 4,469,734 A | 9/1984 | Minto |
| 4,573,986 A | 3/1986 | Minetola et al. |
| 4,610,678 A | 9/1986 | Weisman |
| 4,785,996 A | 11/1988 | Ziecker et al. |
| 4,818,464 A | 4/1989 | Lau |
| 4,834,735 A | 5/1989 | Alemany |
| 4,842,666 A | 6/1989 | Werenicz |
| 4,888,231 A | 12/1989 | Angstadt |
| 5,006,394 A | 4/1991 | Baird |
| 5,037,416 A | 8/1991 | Allen |
| 5,137,537 A | 8/1992 | Herron |
| 5,151,092 A | 9/1992 | Buell |
| 5,260,345 A | 11/1993 | Desmarais |
| 5,269,775 A | 12/1993 | Freeland |
| 5,350,624 A | 9/1994 | Georger |
| 5,387,207 A | 2/1995 | Dyer |
| 5,397,316 A | 3/1995 | Young |
| 5,554,145 A | 9/1996 | Roe |
| 5,569,234 A | 10/1996 | Buell |
| 5,607,760 A | 3/1997 | Roe |
| 5,609,587 A | 3/1997 | Roe |
| 5,625,222 A | 4/1997 | Yoneda |
| 5,628,097 A | 5/1997 | Benson |
| 5,635,191 A | 6/1997 | Roe |
| 5,643,588 A | 7/1997 | Roe |
| 5,916,661 A | 6/1999 | Benson |
| 5,968,025 A | 10/1999 | Roe |
| 6,004,306 A | 12/1999 | Robles |
| 6,107,539 A | 8/2000 | Palumbo et al. |
| 6,545,197 B1 | 4/2003 | Muller et al. |
| 6,645,569 B2 | 11/2003 | Cramer et al. |
| 6,772,708 B2 | 8/2004 | Klofta |
| 6,863,933 B2 | 3/2005 | Cramer et al. |
| 7,112,621 B2 | 9/2006 | Rohrbaugh et al. |
| 7,163,528 B2 | 1/2007 | Christon |
| 7,410,683 B2 | 8/2008 | Curro |
| 7,744,576 B2 | 6/2010 | Busam |
| 8,927,801 B2 | 1/2015 | Klofta |
| 9,072,634 B2 | 7/2015 | Hundorf et al. |
| 9,789,009 B2 | 10/2017 | Joseph |
| 9,808,551 B2 | 11/2017 | Pan |
| 10,206,826 B2 | 2/2019 | Isele |
| 2003/0105190 A1 | 6/2003 | Diehl et al. |
| 2003/0148684 A1 | 8/2003 | Cramer et al. |
| 2004/0158212 A1 | 8/2004 | Ponomarenko et al. |
| 2004/0167486 A1 | 8/2004 | Busam |
| 2005/0008839 A1 | 1/2005 | Cramer et al. |
| 2005/0159720 A1 | 7/2005 | Gentilcore |
| 2008/0312618 A1 | 12/2008 | Hundorf |
| 2009/0306281 A1 | 12/2009 | Tancrede et al. |
| 2011/0250413 A1 | 10/2011 | Lu |
| 2011/0268932 A1 | 11/2011 | Catalan |
| 2011/0274834 A1 | 11/2011 | Brown |
| 2011/0319848 A1 | 12/2011 | Mckiernan |
| 2012/0165771 A1 | 6/2012 | Ruman |
| 2012/0316526 A1 | 12/2012 | Rosati et al. |
| 2014/0257216 A1 | 9/2014 | Gatto |
| 2014/0274870 A1 | 9/2014 | Cetti |
| 2014/0358100 A1 | 12/2014 | Remmers |
| 2015/0283003 A1 | 10/2015 | Rosati |
| 2017/0165133 A1* | 6/2017 | Turner .................. A61F 13/53 |
| 2017/0209616 A1 | 7/2017 | Turner |
| 2019/0110936 A1 | 4/2019 | Becker et al. |
| 2020/0030162 A1 | 1/2020 | Lindner et al. |
| 2024/0000636 A1* | 1/2024 | Lindner ................ B01J 20/264 |

* cited by examiner

ABSORBENT CORES COMPRISING A SUPERABSORBENT POLYMER IMMOBILIZING MATERIAL

CROSS-REFERENCE TO RELATED APPLICATIONS

This application is a continuation of U.S. application Ser. No. 16/520,386, filed on Jul. 24, 2019, which claims the benefit of U.S. Provisional Application No. 62/703,585, filed on Jul. 26, 2018, the entireties of which are all incorporated by reference herein.

FIELD

Described herein is an absorbent core for use in an absorbent article comprising a superabsorbent polymer immobilizing material.

BACKGROUND

Disposable absorbent articles for receiving and retaining bodily discharges such as urine or feces are generally known in the art. Examples of these include disposable diapers, training pants and adult incontinence articles. Typically, disposable diapers comprise a liquid pervious topsheet that faces the wearer's body, a liquid impervious backsheet that faces the wearer's clothing and an absorbent core interposed between the liquid pervious topsheet and the backsheet.

An important component of disposable absorbent articles is the absorbent core structure. The absorbent core structure typically includes a superabsorbent polymer material, such as hydrogel-forming polymer material, also referred to as absorbent gelling material, AGM, or super-absorbent polymer, SAP. This superabsorbent polymer material ensures that large amounts of bodily fluids, e.g., urine, can be absorbed by the absorbent article during its use and be locked away, thus providing low rewet and good skin dryness.

Traditionally, the superabsorbent polymer material is incorporated into the absorbent core structure with cellulose or cellulosic fibres. Now, thinner absorbent core structures can be made by the reduction or elimination of these cellulose fibres from the absorbent core structures, whereby the core structures can still acquire and store large quantities of discharged body fluids, in particular urine. To maintain the mechanical stability of these absorbent core structures, a superabsorbent polymer immobilizing material (SPIM) may be added to stabilize the superabsorbent polymer material. In some cases, this SPIM may be a fiberized structure. The fiberized structure may be an adhesive, that is, a material that has a base polymer, along with other materials such as tackifiers, plasticizers, oils, and/or waxes, for example. However, these additive materials in the fiberized adhesive, other than the base polymer, can migrate during product use and create instability issues that negatively affect the performance and consumer impression of the article and create the need for more adhesive to be used to maintain function. Thus, the use of a fiberized adhesive in the core adds to the cost of the absorbent article and creates stability issues that must be managed. Therefore, there is a need to reduce or eliminate the additive materials in the composition that is used to immobilize the superabsorbent polymer material. Accordingly, there is a need for an immobilizer for the superabsorbent polymer material that is less expensive and that can provide improved stability to the absorbent core.

SUMMARY

Described herein is an absorbent article comprising an absorbent core; wherein the absorbent core comprises a superabsorbent polymer material and a superabsorbent polymer immobilizing material; wherein the superabsorbent polymer immobilizing material comprises from about 20% to about 70% of a first polymer, by weight of the superabsorbent polymer immobilizing material; wherein the superabsorbent polymer immobilizing material comprises from about 30% to about 80% of a second polymer, by weight of the superabsorbent polymer immobilizing material; wherein the first polymer has a peak molecular weight of from about 65,000 g/mol to about 700,000 g/mol, according to the Peak Molecular Weight Test Method described herein; wherein the first polymer is a random and/or block copolymer having ethylene derived units and/or C3-C10 alpha olefin derived units, or the first polymer is a polyolefinic homopolymer having ethylene derived units or propylene derived units or 1-butene derived units, or the first polymer is a styrenic block copolymer; wherein the second polymer has a peak molecular weight of from about 1,000 g/mol to about 60,000 g/mol, according to the Peak Molecular Weight Test Method described herein; wherein the second polymer is a polyolefin; wherein the superabsorbent polymer immobilizing material has a Shear Viscosity at 10 (1/s) at 230° C. of from about 300 mPa·s to about 10,000 mPa·s, according to the Viscosity Rheometry Test Method described herein; and wherein the superabsorbent polymer immobilizing material is substantially free of a tackifier.

Also described herein is an absorbent article comprising an absorbent core; wherein the absorbent core comprises a superabsorbent polymer material and a superabsorbent polymer immobilizing material; wherein the superabsorbent polymer immobilizing material comprises from about 20% to about 70% of a first polymer, by weight of the superabsorbent polymer immobilizing material; wherein the superabsorbent polymer immobilizing material comprises from about 30% to about 80% of a second polymer, by weight of the superabsorbent polymer immobilizing material; wherein the superabsorbent polymer immobilizing material has a Wet Mobilization Value of less than 50%, according to the Wet Mobilization Test Method described herein; wherein the superabsorbent polymer immobilizing material has a Storage Modulus at 100° C. of from about 200 Pa to about 400,000 Pa, according to the Oscillatory Rheometry Test Method described herein; wherein the superabsorbent polymer immobilizing material has a Strain Hardening Index of from about 25 to about 1,000, according to the Strain Hardening Index Test Method described herein; and wherein the superabsorbent polymer immobilizing material has a Shear Viscosity at 10 (1/s) at 230° C. of from about 300 mPa·s to about 10,000 mPa·s, according to the Viscosity Rheometry Test Method described herein.

Also described herein is an absorbent article comprising an absorbent core; wherein the absorbent core comprises a superabsorbent polymer material and a superabsorbent polymer immobilizing material; wherein the superabsorbent polymer immobilizing material comprises from about 20% to about 70% of a first polymer, by weight of the superabsorbent polymer immobilizing material; wherein the superabsorbent polymer immobilizing material comprises from about 30% to about 80% of a second polymer, by weight of the superabsorbent polymer immobilizing material; wherein the first polymer has a peak molecular weight of from about 20,000 g/mol to about 700,000 g/mol, according to the Peak Molecular Weight Test Method described herein; wherein the first polymer is a random and/or block copolymer having ethylene derived units and/or C3-C10 alpha olefin derived units, or the first polymer is a polyolefinic homopolymer having ethylene derived units or propylene derived units or 1-butene derived units, or the first polymer is a styrenic block copolymer; wherein the second polymer has a peak molecular weight of from about 1,000 g/mol to about 90,000 g/mol, according to the Peak Molecular Weight Test Method described herein; wherein the first polymer is different than the second polymer; wherein the superabsorbent polymer immobilizing material has a Shear Viscosity at 10 (1/s) at 230° C. of from about 300 mPa·s to about 10,000 mPa·s, according to the Viscosity Rheometry Test Method described herein; wherein the superabsorbent polymer immobilizing material has a Strain Hardening Index of from about 25 to about 1,000, according to the Strain Hardening Index Test Method described herein; and wherein the superabsorbent polymer immobilizing material is substantially free of a tackifier.

DETAILED DESCRIPTION

Definitions

Figure 1:
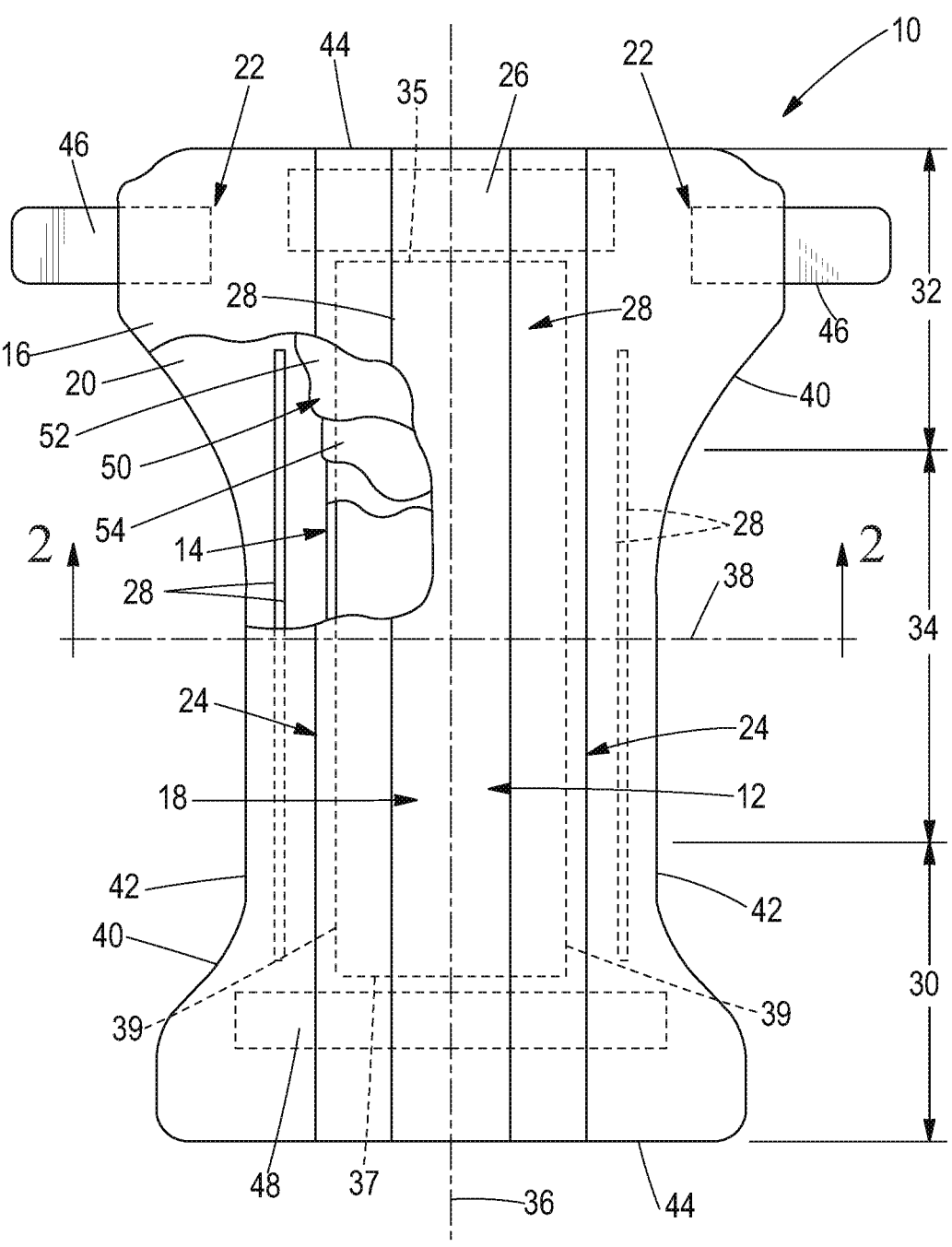
FIG. 1 is a plan view of an exemplary diaper in accordance with the absorbent article described herein.

"Absorbent article", as used herein, refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" or "absorbent structure", as used herein, means a structure typically disposed between a topsheet and backsheet of an absorbent article for absorbing and containing liquid received by the absorbent article and may comprise one or more substrates, absorbent polymer material disposed on the one or more substrates, and a thermoplastic composition, such as a superabsorbent polymer immobilizing material, on the superabsorbent particulate polymer material and at least a portion of the one or more substrates for immobilizing the superabsorbent particulate polymer material on the one or more substrates. In a multilayer absorbent core, the absorbent core may also include a cover layer. The one or more substrates and the cover layer may comprise a nonwoven. Further, the absorbent core may be substantially cellulose free. The absorbent core does not include an acquisition system, a topsheet, or a backsheet of the absorbent article. The absorbent core may consist essentially of the one or more substrates, the absorbent polymer material, a superabsorbent polymer immobilizing material that may be a fiberized structure, and optionally the cover layer.

"Airfelt", as used herein, refers to comminuted wood pulp, which is a form of cellulosic fiber.

"Comprise," "comprising," and "comprises", as used herein, are open ended terms, each specifies the presence of what follows, e.g., a component, but does not preclude the presence of other features, e.g., elements, steps, components known in the art, or disclosed herein.

"Consisting essentially of", as used herein, limits the scope of subject matter, such as that in a claim, to the specified materials or steps and those that do not materially affect the basic and novel characteristics of the subject matter.

"Diaper", as used herein, refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Disposable", as used herein, is used in its ordinary sense to mean an article that is disposed or discarded after a limited number of usage events over varying lengths of time, for example, less than 20 events, less than 10 events, less than 5 events, or less than 2 events.

"Fiber" and "filament", as used herein, are used interchangeably.

"Fiberized structure", as used herein, is understood to comprise a polymer composition from which strands or a net structure is formed and applied to the superabsorbent polymer material with the intent to immobilize the superabsorbent polymer material in both the dry and wet state. The fiberized structure described herein forms a fibrous network over, around, and/or between the superabsorbent polymer material.

"Nonwoven", as used herein, is a manufactured sheet, web, or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than 0.001 mm to greater than 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants".

"Substantially", as used herein, means generally the same or uniform but allowing for or having minor fluctuations from a defined property, definition, etc. For example, small measurable or immeasurable fluctuations in a measured property described herein, such as viscosity, melting point, etc. may result from human error or methodology precision. Other fluctuations are caused by inherent variations in the manufacturing process, thermal history of a formulation, and the like. The compositions of the present invention, nonetheless, would be said to be substantially having the property as reported.

"Substantially cellulose free", as used herein, describes an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substrate", as used herein, means any item having at least a partially or fully solidified fiber or planar surface. In some cases, a single substrate may be positioned in a way that it is referred to as two or more substrates; for example, a folded film or folded nonwoven, or two sides of a cardboard sheet folded over, wherein the two sides are adhesively bonded together. The substrates can be impermeable, permeable, porous or nonporous.

"Superabsorbent particulate polymer material", as used herein, refers to a superabsorbent polymer material which is in particulate form so as to be flowable in the dry state.

Figure 8:
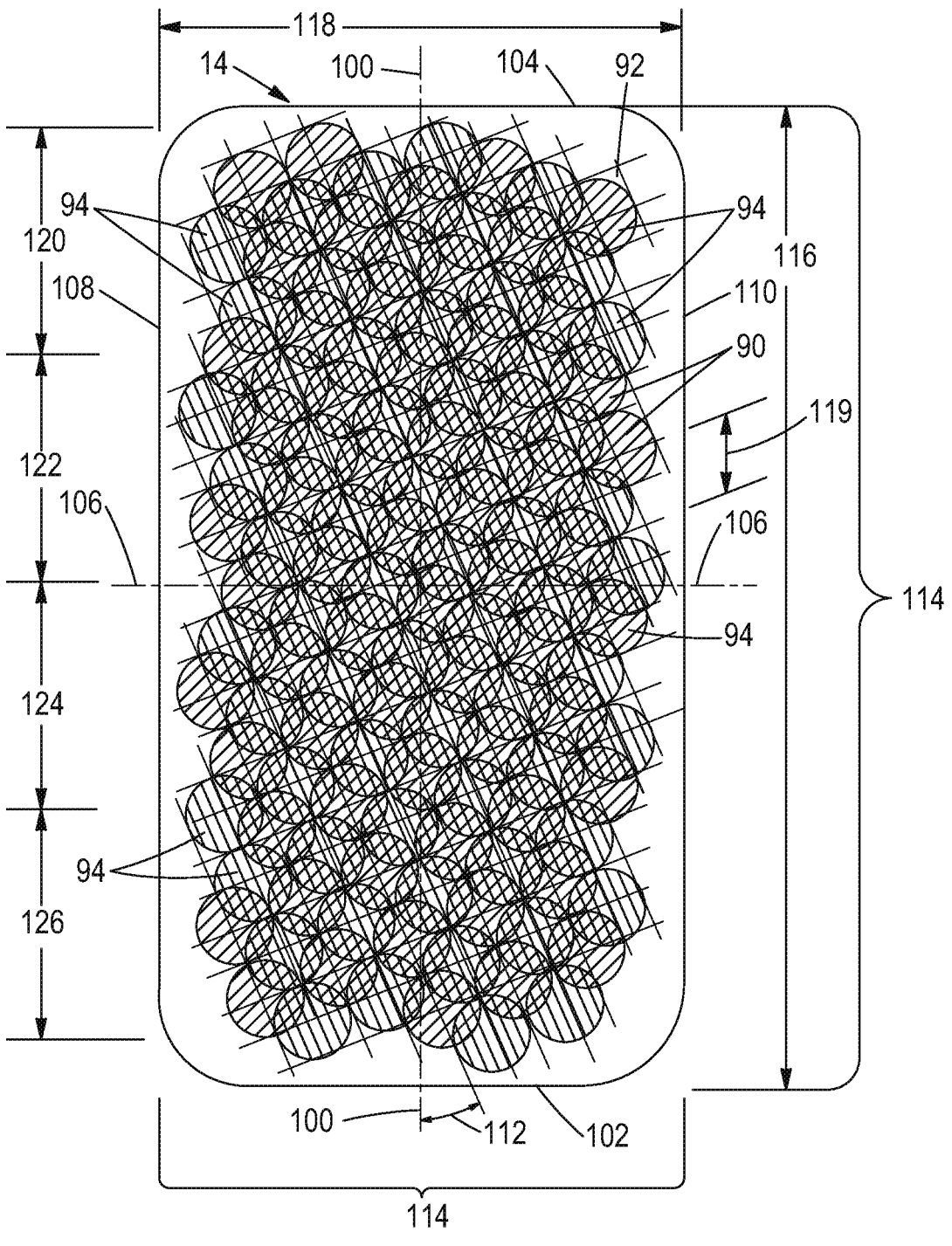
FIG. 8 is a plan view of the absorbent core illustrated in FIGS. 7a and 7b.

"Superabsorbent particulate polymer material area", as used herein, refers to the area of the core wherein the first substrate and second substrate are separated by a multiplicity of superabsorbent particles. In FIG. 8, the boundary of the superabsorbent particulate polymer material area is defined by the perimeter of the overlapping circles. There may be some extraneous superabsorbent particles outside of this perimeter between the first substrate and second substrate.

"Superabsorbent polymer immobilizing material" or "SPIM", as used herein, means a composition that is applied to the superabsorbent polymer material with the intent to immobilize the superabsorbent polymer material in both the dry and wet state. The SPIM may be a fiberized structure with, for example, microfibers or nanofibers, or may be a film, discrete blobs of material, or some other form.

"Superabsorbent polymer material", "absorbent polymer material," "absorbent gelling material," "AGM," and "superabsorbent material", as used herein, are used interchangeably and refer to cross linked polymeric materials that can absorb at least 5 times their weight of an aqueous 0.9% saline solution as measured using the Centrifuge Retention Capacity test (Edana 441.2-01).

Absorbent Article

FIG. 1 is a plan view of an absorbent article, such as a diaper, 10. The diaper 10 is shown in its flat out, uncontracted state (i.e., without elastic induced contraction) and portions of the diaper 10 are cut away to more clearly show the underlying structure of the diaper 10. A portion of the diaper that contacts a wearer is facing the viewer in FIG. 1. The diaper 10 generally may comprise a chassis 12 and an absorbent core 14 disposed in the chassis.

The chassis 12 of the diaper 10 in FIG. 1 may comprise the main body of the diaper 10. The chassis 12 may comprise an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its longitudinal axis 36 and its transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 10 may also include such other features as are known in the art including front and rear ear panels, waist cap features, elastics and the like to provide better fit, containment and aesthetic characteristics. Such additional features are well known in the art and are e.g., described in U.S. Pat. Nos. 3,860,003 and 5,151,092.

In order to keep the diaper 10 in place about the wearer, at least a portion of the first waist region 30 may be attached by the fastening member 46 to at least a portion of the second waist region 32 to form leg opening(s) and an article waist. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements.

The diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. The materials making up the fastening device may be flexible. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the topsheet 18, the backsheet 20, and the absorbent core 14 may be assembled in a variety of well-known configurations, exemplary diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 18 in FIG. 1 may be fully or partially elasticized or may be foreshortened to provide a void space between the topsheet 18 and the absorbent core 14. Exemplary structures including elasticized or foreshortened topsheets are described in more detail in U.S. Pat. Nos. 5,037, 416 and 5,269,775.

The topsheet may be compliant, soft feeling, and non-irritating to the wearer's skin and may be elastically stretchable in one or more directions. Further, the topsheet may be liquid pervious, permitting liquids (e.g., menses, urine, and/or runny feces) to penetrate through its thickness. Various topsheets may also comprise a hydrophilic material, for example, which is configured to draw bodily fluids into an absorbent core of the chassis when these fluids are expelled from the body. A suitable topsheet may be manufactured from a wide range of materials, such as woven and nonwoven materials, apertured or hydroformed thermoplastic films, apertured nonwovens, porous foams, reticulated foams, reticulated thermoplastic films, and/or thermoplastic scrims, for example. Suitable apertured films may comprise those described in U.S. Pat. Nos. 3,929,135, 4,324,246, 4,342,314, 4,463,045, 5,006,394, 5,628,097, 5,916,661, 6,545,197, and 6,107,539.

Apertured film or nonwoven topsheets typically may be pervious to bodily exudates, yet non-absorbent, and have a reduced tendency to allow fluids to pass back through and rewet the wearer's skin. Suitable woven and nonwoven materials may comprise natural fibers, such as, for example, wood or cotton fibers, synthetic fibers, such as, for example, polyester, polypropylene, or polyethylene fibers, or combinations thereof. If the topsheet comprises fibers, the fibers may be spunbond, carded, wet-laid, meltblown, hydroentangled, or otherwise processed, for example, as is generally known in the art.

The topsheet may comprise a skin care lotion. Examples of suitable lotions include, but are not limited to, those described in U.S. Pat. Nos. 5,607,760; 5,609,587; 5,635, 191; 5,643,588; and 5,968,025, and as described in U.S. Application No. 61/391,353, and as described in U.S. Pub. No. 2014-0257216. Beyond these compositions, the absorbent article may comprise soluble cyclodextrin derivatives such as those described in U.S. Pub. No. 2014/0274870.

Additionally, the topsheet of the present disclosure may be a tufted laminate web as disclosed in U.S. Pat. No. 7,410,683, and/or may be an apertured web as disclosed in PCT/CN2014/083769 having an international filing date of Aug. 6, 2014.

The topsheet may comprise graphics such that depth perception is created as described in U.S. Pat. No. 7,163, 528. The topsheet may be an integrated acquisition layer and topsheet as described in U.S. Ser. No. 14/680,426 or 14/634, 928.

The absorbent article may comprise a backsheet. The backsheet may be impervious, or at least partially impervious, to fluids or body exudates (e.g., menses, urine, and/or runny feces) and may be manufactured from a thin plastic film, although other flexible liquid impervious materials may also be used. The backsheet may prevent the body exudates or fluids absorbed and contained in an absorbent core of the absorbent article from wetting articles which contact the absorbent article, such as bedsheets, pajamas, clothes, and/or undergarments. The backsheet may comprise a woven or nonwoven material, polymeric films such as thermoplastic films of polyethylene or polypropylene, and/ or a multi-layer or composite materials comprising a film and a nonwoven material (e.g., having an inner film layer and an outer nonwoven layer). A suitable backsheet may comprise a polyethylene film having a thickness of from about 0.012 mm (0.5 mils) to about 0.051 mm (2.0 mils). Examples of polyethylene films are manufactured by Clopay Corporation of Cincinnati, Ohio, under the designation BR-120 and BR-121, and by Tredegar Film Products of Terre Haute, Ind., under the designation XP-39385.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m2 to about 35 g/m2. The backsheet can be typically positioned adjacent the outer-facing surface of the absorbent core and can be joined thereto. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986. Another suitable attachment device including several lines of adhesive filaments swirled into a spiral pattern is illustrated by the apparatus and methods shown in U.S. Pat. Nos. 3,911,173; 4,785,996; and 4,842,666. Alternatively, the attachment device may include heat bonds, pressure bonds, ultrasonic bonds, dynamic mechanical bonds, or any other suitable attachment device or combinations of these attachment devices.

The backsheet may be embossed and/or matte-finished to provide a more cloth-like appearance. Further, the backsheet may permit vapors to escape from the absorbent core of the absorbent article (i.e., the backsheet is breathable) while still preventing, or at least inhibiting, fluids or body exudates from passing through the backsheet. The size of the backsheet may be dictated by the size of the absorbent article and the design or configuration of the absorbent article to be formed, for example.

The backsheet 20 may be joined with the topsheet 18. Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995, in the name of E. I. DuPont, which is hereby incorporated by reference. Other breathable backsheets including nonwoven webs and apertured formed films are described in U.S. Pat. No. 5,571,096 issued to Dobrin et al. on Nov. 5, 1996, which is hereby incorporated by reference.

The backsheet may have a water vapor transmission rate (WVTR) of greater than 2,000 g/24 h/m$^2$, greater than 3,000 g/24 h/m$^2$, greater than 5,000 g/24 h/m$^2$, greater than 6,000 g/24 h/m$^2$, greater than 7,000 g/24 h/m$^2$, greater than 8,000 g/24 h/m$^2$, greater than 9,000 g/24 h/m$^2$, greater than 10,000 g/24 h/m$^2$, greater than 11,000 g/24 h/m$^2$, greater than 12,000 g/24 h/m$^2$, greater than 15,000 g/24 h/m$^2$, measured according to WSP 70.5 (08) at 37.8° C. and 60% relative humidity.

Figure 2:
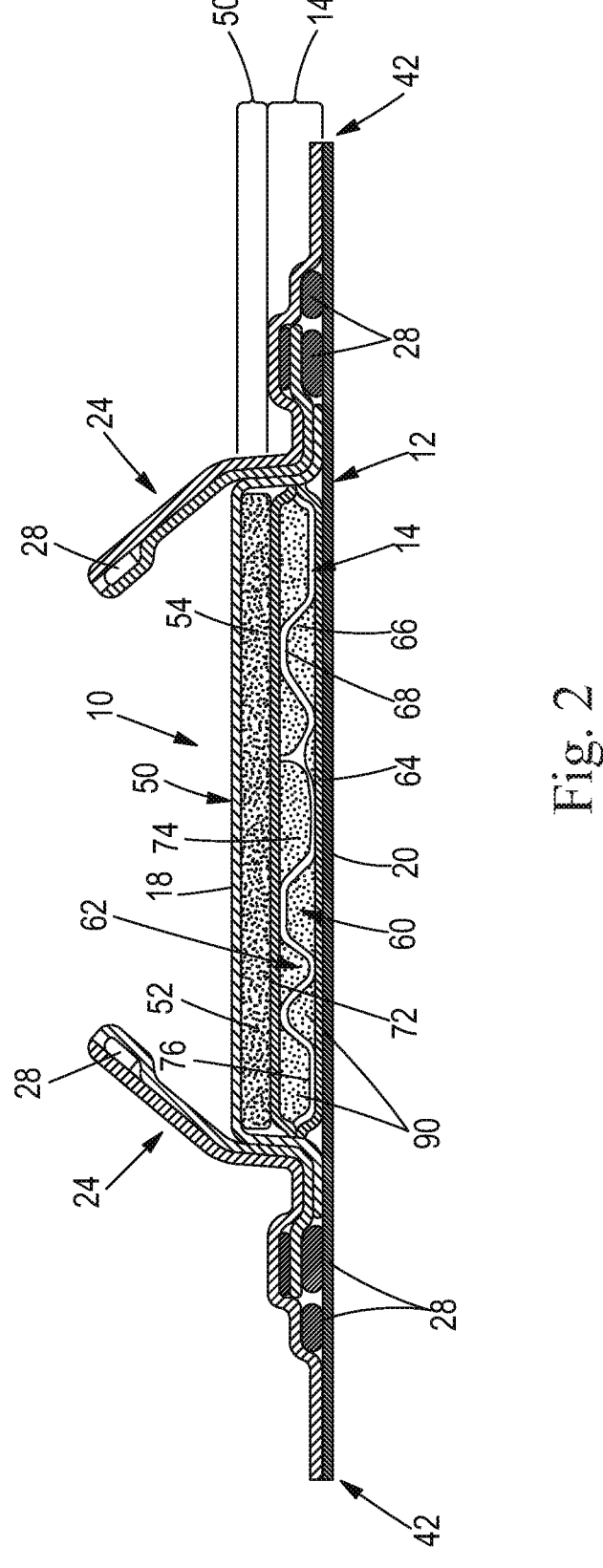
FIG. 2 is a cross sectional view of the diaper shown in FIG. 1 taken along the sectional line 2-2 of FIG. 1.

FIG. 2 shows a cross section of FIG. 1 taken along the sectional line 2-2 of FIG. 1. Starting from the wearer facing side, the diaper 10 may comprise the topsheet 18, the components of the absorbent core 14, and the backsheet 20. The diaper 10 may also comprise an acquisition system 50 disposed between the liquid permeable topsheet 18 and a wearer facing side of the absorbent core 14. The acquisition system 50 may be in direct contact with the absorbent core. The acquisition system 50 may comprise a single layer or multiple layers, such as an upper acquisition layer 52 facing towards the wearer's skin and a lower acquisition 54 layer facing the garment of the wearer. The acquisition system 50 may function to receive a surge of liquid, such as a gush of urine. In other words, the acquisition system 50 may serve as a temporary reservoir for liquid until the absorbent core 14 can absorb the liquid.

The acquisition system 50 may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. The cross-linked cellulosic fibers may be crimped, twisted, or curled, or a combination thereof including crimped, twisted, and curled.

One or both of the upper and lower acquisition layers 52 and 54 may comprise a nonwoven, which may be hydrophilic. One or both of the upper and lower acquisition layers 52 and 54 may comprise the chemically cross-linked cellulosic fibers, which may or may not form part of a nonwoven material. The upper acquisition layer 52 may comprise a nonwoven, without the cross-linked cellulosic fibers, and the lower acquisition layer 54 may comprise the chemically cross-linked cellulosic fibers. The lower acquisition layer 54 may comprise the chemically cross-linked cellulosic fibers mixed with other fibers such as natural or synthetic polymeric fibers. Such other natural or synthetic polymeric fibers may include high surface area fibers, thermoplastic binding fibers, polyethylene fibers, polypropylene fibers, PET fibers, rayon fibers, lyocell fibers, and mixtures thereof. The lower acquisition layer 54 has a total dry weight, the cross-linked cellulosic fibers are present on a dry weight basis in the upper acquisition layer in an amount from about 30% to about 95% by weight of the lower acquisition layer 54, and the other natural or synthetic polymeric fibers are present on a dry weight basis in the lower acquisition layer 54 in an amount from about 70% to about 5% by weight of the lower acquisition layer 54.

The lower acquisition layer 54 desirably has a high fluid uptake capability. Fluid uptake is measured in grams of absorbed fluid per gram of absorbent material and is expressed by the value of "maximum uptake." A high fluid uptake corresponds therefore to a high capacity of the material and is beneficial, because it ensures the complete acquisition of fluids to be absorbed by an acquisition material. The lower acquisition layer 54 has a maximum uptake of about 10 g/g.

Suitable nonwoven materials for the upper and lower acquisition layers 52 and 54 include, but are not limited to SMS material, comprising a spunbonded, a melt-blown and a further spunbonded layer. Permanently hydrophilic nonwovens, and in particular, nonwovens with durably hydrophilic coatings may be desirable. The nonwoven materials may be formed by a nonwoven web, such as a carded nonwoven, a spunbond nonwoven ("S") or a meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1, or US2011/0250413A1. Nonwoven materials provided from synthetic fibers may be used, such as polyethylene, polyethylene terephthalate, and in particular polypropylene.

As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720, which is hereby incorporated by reference. Another way to produce nonwovens with durably hydrophilic coatings is to coat the nonwoven with hydrophilic nanoparticles as described in applications U.S. Pat. No. 7,112,621 to Rohrbaugh et al. and in PCT Application Publication WO 02/064877, which are hereby incorporated by reference.

Typically, nanoparticles have a largest dimension of below 750 nm. Nanoparticles with sizes ranging from 2 nm to 750 nm may be economically produced. An advantage of nanoparticles is that many of them can be easily dispersed in water solution to enable coating application onto the non-woven, they typically form transparent coatings, and the coatings applied from water solutions are typically suffi-ciently durable to exposure to water. Nanoparticles can be organic or inorganic, synthetic or natural. Inorganic nan-oparticles generally exist as oxides, silicates, and/or, car-bonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). A suitable nanoparticle coated nonwoven is that disclosed in U.S. patent application Ser. No. 10/758,066 entitled "Disposable absorbent article comprising a durable hydrophilic core wrap" to Ekaterina Anatolyevna Ponomarenko and Mattias NMN Schmidt, which is hereby incorporated by reference.

Further useful nonwovens are described in U.S. Pat. No. 6,645,569 to Cramer et al., U.S. Pat. No. 6,863,933 to Cramer et al., U.S. Pat. No. 7,112,621 to Rohrbaugh et al., and co-pending patent application Ser. No. 10/338,603 to Cramer et al. and Ser. No. 10/338,610 to Cramer et al., which are hereby incorporated by reference.

In some cases, the nonwoven surface can be pre-treated with high energy treatment (corona, plasma) prior to appli-cation of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic nonwovens are also useful in other parts of an absorbent article. For example, topsheets and absorbent core layers comprising permanently hydrophilic nonwovens as described above have been found to work well.

The upper acquisition layer 52 may comprise a material that provides good recovery when external pressure is applied and removed. Further, the upper acquisition layer 52 may comprise a blend of different fibers selected, for example from the types of polymeric fibers described above. At least a portion of the fibers may exhibit a spiral-crimp which has a helical shape. The upper acquisition layer 52 may comprise fibers having different degrees or types of crimping, or both. The upper acquisition layer may include a mixture of fibers having about 8 crimps per inch (cpi) to about 12 cpi, or about 9 cpi to about 10 cpi, and other fibers having about 4 cpi to about 8 cpi, or about 5 to about 7 cpi. Different types of crimps include, but are not limited to a 2D crimp or "flat crimp" and a 3D or spiral-crimp. The fibers may include bi-component fibers, which are individual fibers each comprising different materials, usually a first and a second polymeric material. It is believed that the use of side-by-side bi-component fibers is beneficial for imparting a spiral-crimp to the fibers.

The upper acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). The binder may be present in the upper acquisition layer 52 in excess of about 12%, about 14% or about 16% by weight. Exemplary SB latex is available under the trade name GENFLO™ 3160 (OM-NOVA Solutions Inc.; Akron, Ohio).

Absorbent Core

Figure 3:
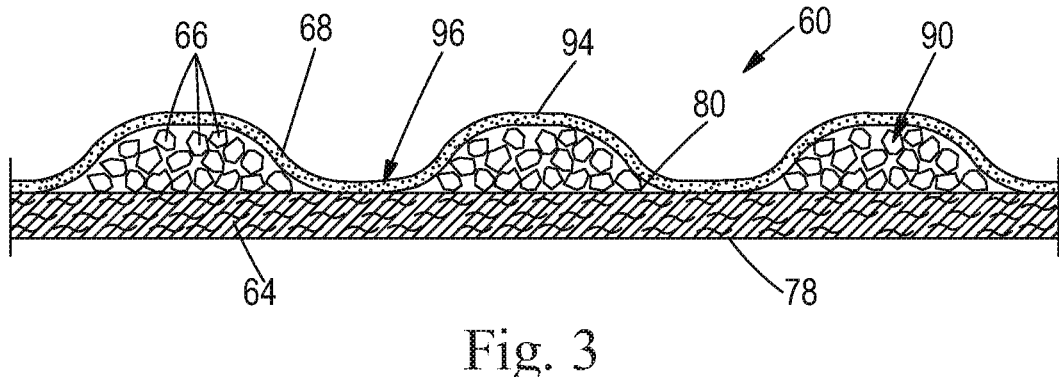
FIG. 3 is a partial cross sectional view of an exemplary absorbent core layer in accordance with the absorbent article described herein.

The absorbent core 14 in FIGS. 1-8 generally is disposed between the topsheet 18 and the backsheet 20 and may comprise two layers, a first absorbent layer 60 and a second absorbent layer 62. As best shown in FIG. 3, the first absorbent layer 60 of the absorbent core 14 comprises a substrate 64, an superabsorbent particulate polymer material (such as a superabsorbent polymer material) 66 deposited on the substrate 64, and a superabsorbent polymer immobiliz-ing material, (SPIM), 68 on the superabsorbent particulate polymer material 66 and at least portions of the first sub-strate 64 as a means for covering and immobilizing the superabsorbent particulate polymer material 66 on the first substrate 64. The superabsorbent polymer immobilizing material may be a thermoplastic composition and/or may be a fiberized structure. According to FIG. 4, the first absorbent layer 60 of the absorbent core 14 may also include a cover layer 70 on the SPIM 68.

Likewise, as best illustrated in FIG. 2, the second absor-bent layer 62 of the absorbent core 14 may also include a substrate 72, an superabsorbent particulate polymer material (such as a superabsorbent polymer material) 74 on the second substrate 72, and a SPIM that may be a thermoplastic composition and/or a fiberized structure 76 on the superab-sorbent particulate polymer material 74 and at least a portion of the second substrate 72 for immobilizing the superabsor-bent particulate polymer material 74 on the second substrate 72. Although not illustrated, the second absorbent layer 62 may also include a cover layer such as the cover layer 70 illustrated in FIG. 4. The first and second absorbent layers may be combined together such that at least a portion of the superabsorbent polymer immobilizing material of the first absorbent layer contacts at least a portion of the superab-sorbent polymer immobilizing material of the second absor-bent layer.

The substrate 64 of the first absorbent layer 60 may be a dusting layer or a core cover, and has a first surface or outer surface 78 which faces the backsheet 20 of the diaper 10 and a second surface or inner surface 80 which faces the super-absorbent particulate polymer material 66. Likewise, the substrate 72 of the second absorbent layer 62 may be referred to as a core cover and has a first surface or outer surface 82 facing the topsheet 18 of the diaper 10 and a second surface or inner surface 84 facing the superabsorbent particulate polymer material 74. The first substrate 64 and the second substrate 72 may both be core covers or core wrap material. The first and second substrates 64 and 72 may be adhered to one another with adhesive about the periphery to form an envelope about the superabsorbent particulate polymer materials 66 and 74 to hold the superabsorbent particulate polymer material 66 and 74 within the absorbent core 14. The absorbent core may then have a front edge 35, a back edge 37, and two side edges 39. The bonded periphery at the front edge 35 may form a front end seal and the bonded periphery at the back edge may form a back end seal.

The substrates 64 and 72 of the first and second absorbent layers 60 and 62 may be a nonwoven material, such as those nonwoven materials described above. The nonwovens are porous and may have a pore size of about 32 microns.

As illustrated in FIGS. 1-8, the superabsorbent particulate polymer material 66 and 74 is deposited on the respective substrates 64 and 72 of the first and second absorbent layers 60 and 62 in clusters 90 of particles to form a grid pattern 92 comprising land areas 94 and junction areas 96 between the land areas 94. As defined herein, land areas 94 are areas where the SPIM does not contact the nonwoven substrate or the auxiliary adhesive (discussed below) directly; junction areas 96 are areas where the SPIM does contact the non-woven substrate or the auxiliary adhesive directly. The junction areas 96 in the grid pattern 92 contain little or no superabsorbent particulate polymer material 66 and 74. The land areas 94 and junction areas 96 can have a variety of shapes including, but not limited to, circular, oval, square, rectangular, triangular, and the like.

The grid pattern shown in FIG. 8 is a square grid with regular spacing and size of the land areas. Other grid patterns including hexagonal, rhombic, orthorhombic, parallelogram, triangular, rectangular, and combinations thereof may also be used. The spacing between the grid lines may be regular or irregular.

The size of the land areas 94 in the grid patterns 92 may vary. The width 119 of the land areas 94 in the grid patterns 92 ranges from about 8 mm to about 12 mm. The width of the land areas 94 is about 10 mm. The junction areas 96, on the other hand, may have a width or larger span of less than 5 mm, less than 3 mm, less than 2 mm, less than 1.5 mm, less than 1 mm, or less than 0.5 mm.

As shown in FIG. 8, the absorbent core 14 has a longitudinal axis 100 extending from a rear end 102 to a front end 104 and a transverse axis 106 perpendicular to the longitudinal axis 100 extending from a first edge 108 to a second edge 110. The grid pattern 92 of superabsorbent particulate polymer material clusters 90 is arranged on the substrates 64 and 72 of the respective absorbent layers 60 and 62 such that the grid pattern 92 formed by the arrangement of land areas 94 and junction areas 96 forms a pattern angle 112. The pattern angle 112 may be 0 degrees, greater than 0 degrees, or from about 15 degrees to about 30 degrees, or from about 5 degrees to about 85 degrees, or from about 10 degrees to about 60 degrees, or from about 15 degrees to about 30 degrees.

Figures 7A, 7B:
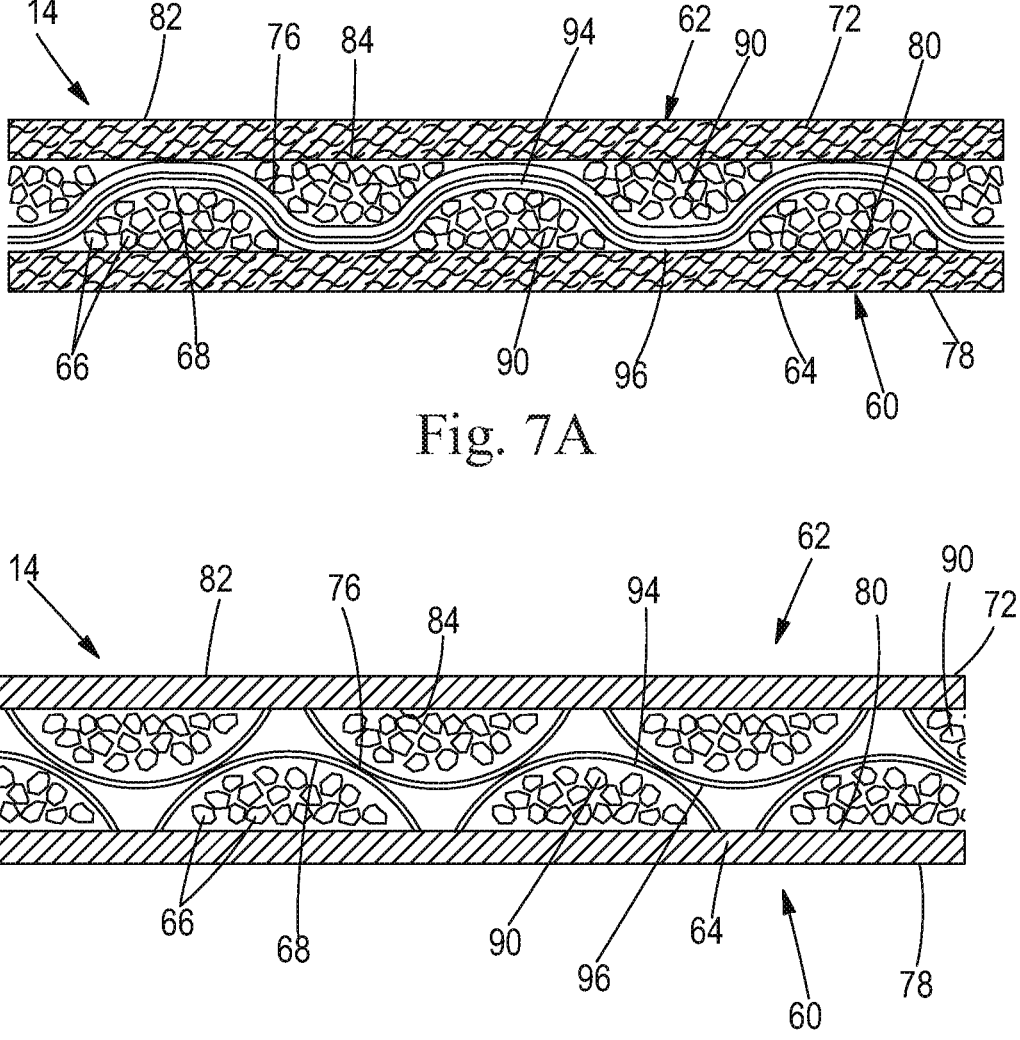
FIG. 7A is a partial sectional view of an exemplary absorbent core comprising a combination of the first and second absorbent core layers illustrated in FIGS. 5 and 6.
FIG. 7B is a partial sectional view of an exemplary absorbent core comprising a combination of the first and second absorbent core layers illustrated in FIGS. 5 and 6.

As best seen in FIGS. 7a, 7b, and 8, the first and second layers 60 and 62 may be combined to form the absorbent core 14. The absorbent core 14 has a superabsorbent polymer material area (or superabsorbent particulate area) 114 bounded by a pattern length 116 and a pattern width 118. The extent and shape of the superabsorbent polymer material area 114 may vary depending on the desired application of the absorbent core 14 and the particular absorbent article in which it may be incorporated. The superabsorbent polymer material area 114 may extend substantially entirely across the absorbent core 14, such as is illustrated in FIG. 8.

The first and second absorbent layers 60 and 62 may be combined together to form the absorbent core 14 such that the grid patterns 92 of the respective first and second absorbent layers 62 and 64 are offset from one another along the length and/or width of the absorbent core 14. The respective grid patterns 92 may be offset such that the superabsorbent polymer material 66 and 74 is substantially continuously distributed across the superabsorbent polymer area 114. The superabsorbent polymer material (or superabsorbent particulate polymer material) 66 and 74 is substantially continuously distributed across the superabsorbent particulate polymer material area 114 despite the individual grid patterns 92 comprising superabsorbent particulate polymer material 66 and 74 discontinuously distributed across the first and second substrates 64 and 72 in clusters 90. The grid patterns may be offset such that the land areas 94 of the first absorbent layer 60 face the junction areas 96 of the second absorbent layer 62 and the land areas 94 of the second absorbent layer 62 face the junction areas 96 of the first absorbent layer 60. When the land areas 94 and junction areas 96 are appropriately sized and arranged, the resulting combination of superabsorbent particulate polymer material 66 and 74 is a substantially continuous layer of superabsorbent particular polymer material across the superabsorbent particulate polymer material area 114 of the absorbent core 14 (i.e. first and second substrates 64 and 72 do not form a plurality of pockets, each containing a cluster 90 of superabsorbent particulate polymer material 66 therebetween). Respective grid patterns 92 of the first and second absorbent layer 60 and 62 may be substantially the same.

As shown in FIG. 8, the amount of superabsorbent particulate polymer material 66 and 74 may vary along the length 116 of the grid pattern 92. The grid pattern may be divided into absorbent zones 120, 122, 124, and 126, in which the amount of superabsorbent particulate polymer material 66 and 74 varies from zone to zone. As used herein, "absorbent zone" refers to a region of the superabsorbent particulate polymer material area having boundaries that are perpendicular to the longitudinal axis shown in FIG. 8. The amount of superabsorbent particulate polymer material 66 and 74 may gradually transition from one of the plurality of absorbent zones 120, 122, 124, and 126 to another. This gradual transition in amount of superabsorbent particulate polymer material 66 and 74 may reduce the possibility of cracks forming in the absorbent core 14.

The amount of superabsorbent particulate polymer material 66 and 74 present in the absorbent core 14 may vary, but may be present in the absorbent core in an amount greater than 80% by weight of the absorbent core, or greater than 85% by weight of the absorbent core, or greater than 90% by weight of the absorbent core, or greater than 95% by weight of the core. The absorbent core 14 may consist essentially of the first and second substrates 64 and 72, the superabsorbent particulate polymer material 66 and 74, and the SPIM 68 and 76. The absorbent core may have three or more absorbent layers. The absorbent core 14 may be substantially cellulose free.

The weight of superabsorbent particulate polymer material 66 and 74 in at least one freely selected first square measuring 1 cm×1 cm may be at least 10%, or 20%, or 30%, 40% or 50% higher than the weight of superabsorbent particulate polymer material 66 and 74 in at least one freely selected second square measuring 1 cm×1 cm. The first and the second square are centered about the longitudinal axis.

The superabsorbent particulate polymer material area may have a relatively narrow width in the crotch area of the absorbent article for increased wearing comfort. Hence, the superabsorbent particulate polymer material area may have a width as measured along a transverse line which is positioned at equal distance to the front edge and the rear edge of the absorbent article, which is less than 100 mm, 90 mm, 80 mm, 70 mm, 60 mm or even less than 50 mm.

It has been found that, for most absorbent articles such as diapers, the liquid discharge occurs predominately in the front half of the diaper. The front half of the absorbent core 14 should therefore comprise most of the absorbent capacity of the core. Thus, the front half of said absorbent core 14 may comprise greater than 60% of the superabsorbent polymer material, or greater than 65%, 70%, 75%, 80%, 85%, or 90% of the superabsorbent polymer material.

The absorbent core may comprise a core wrap enclosing the absorbent material. The core wrap may be both the first and second substrates. The core wrap may be formed by two substrates, typically nonwoven material which may be at least partially sealed along the sides of the absorbent core. The first nonwoven may substantially form the top side of the core wrap and the second nonwoven substantially the bottom side of the core wrap. The core wrap may be at least partially sealed along its front side, back side and/or two longitudinal sides to improve the containment of the absorbent material during use. A C-wrap seal may be for example provided on the longitudinal sides of the core if improved containment is desired. Exemplary C-wrap description may be found in U.S. application Ser. No. 14/560,211, which is hereby incorporated by reference. Typical core wraps comprise two substrates (216 and 216' in FIG. 11) which are attached to another, but the core wrap may also be made of a single substrate folded around the absorbent material, or may comprises several substrates. When two substrates are used, these may be typically attached to another along at least part of the periphery of the absorbent core to form a seal. Typically neither first nor second substrates need to be shaped, so that they can be rectangularly cut for ease of production but other shapes are not excluded.

Figure 11:
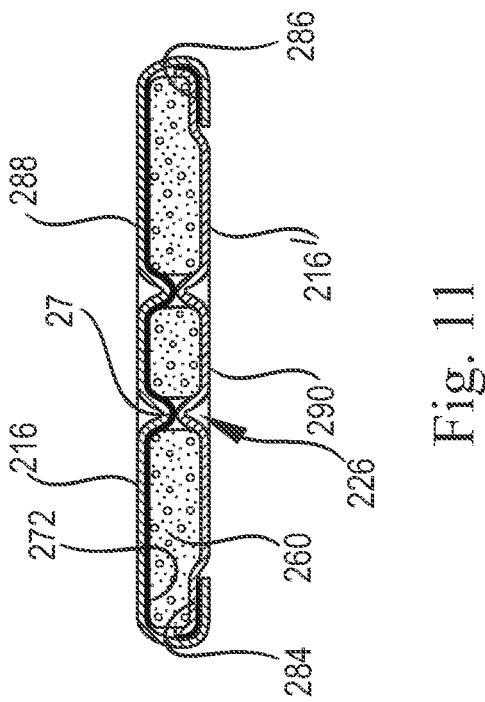
FIG. 11 is a transversal cross-section of the core of FIG. 10 along 2-2.

The substrates are advantageously attached to another to form a seal along all the edges of the core. Typical seals are the so-called C-wrap and sandwich wrap. In a C-wrap, such as shown in FIG. 11, one of the substrate, e.g., the first substrate 216, has flaps extending over the opposed edges of the core which are then folded over the other substrate. These flaps are bonded to the external surface of the other substrate, typically by adhesive. This so called C-wrap construction can provide benefits such as improved resistance to bursting in a wet loaded state compared to a sandwich seal.

The front side and back side of the core wrap may then also be sealed for example by adhering the first substrate and second substrate to another to provide complete enclosing of the absorbent material across the whole of the periphery of the core. For the front side and back side of the core, the first and second substrate may extend and be joined together in a substantially planar direction, forming a so-called sandwich construction. In the so-called sandwich seal construction, the first and second substrates both have material extension outwardly of the absorbent material deposition area which are then sealed flat along the whole or parts of the periphery of the core typically by gluing and/or heat/pressure bonding.

The terms "seal" and "enclosing" are to be understood in a broad sense. The seal does not need to be continuous along the whole periphery of the core wrap but may be discontinuous along part or the whole of it, such as formed by a series of seal points spaced on a line. Typically, a seal may be formed by gluing and/or thermal bonding. The core wrap may also be formed by a single substrate which may enclose the absorbent material as in a parcel wrap and be for example sealed along the front side and back side of the core and one longitudinally extending seal.

The core wrap may be formed by any materials suitable for enclosing the absorbent material. Typical substrate materials used in the production of conventional cores may be used, in particular nonwovens but also paper, tissues, films, wovens, or laminate of any of these. The core wrap may in particular be formed by a nonwoven web, such as a carded nonwoven, a spunbond nonwoven ("S") or a meltblown nonwoven ("M"), and laminates of any of these. For example, spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1, or US2011/0250413A1. Nonwoven materials provided from synthetic fibers may be used, such as polyethylene, Polyethylene terephthalate, and in particular polypropylene.

The absorbent core 14 may further comprise any absorbent material that is generally compressible, conformable, non-irritating to the wearer's skin, and capable of absorbing and retaining liquids such as urine and other certain body exudates. The absorbent core 14 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or crosslinked cellulosic fibers, tissue, including tissue wraps and tissue laminates, absorbent foams, absorbent sponges, or any other known absorbent material or combinations of materials. Co-form nonwoven webs or co-form materials are known in the art and have been used in a wide variety of applications, including wipes. The term "co-form material" means a composite material containing a mixture or stabilized matrix of thermoplastic filaments and at least one additional material, often called the "second material" or "secondary material". Examples of the second material include, for example, absorbent fibrous organic materials such as woody and non-wood pulp from, for example, cotton, rayon, recycled paper, pulp fluff; superabsorbent polymer materials such as superabsorbent particles and fibers; inorganic absorbent materials and treated polymeric staple fibers, and other materials such as non-absorbent staple fibers and non-absorbent particles and the like. Exemplary co-form materials are disclosed in commonly assigned U.S. Pat. No. 5,350,624 to Georger et al.; U.S. Pat. No. 4,100,324 to Anderson et al.; U.S. Pat. No. 4,469,734 to Minto; and U.S. Pat. No. 4,818,464 to Lau et al., which are hereby incorporated by reference.

The absorbent core 14 may further comprise minor amounts (typically less than 10%) of materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.), which are hereby incorporated by reference.

As described, the absorbent core may comprise a first and second substrate layer that may partially enclose an absorbent layer comprising superabsorbent polymer. One or both substrates may not be considered to be part of the absorbent core. Either or both of the substrates and/or the absorbent core may be "shaped," meaning non-rectangular. One or both substrates and/or the absorbent core may have an I-beam shape, a "T" shape, an hourglass shape, a dumbbell shape, a mushroom shape, or any suitable shape. The absorbent core may have a central region, a front end region and a back end region, wherein the core has an average width in the central region and a relatively wider average width in at least one of the end regions. The absorbent core may be both formed and shaped on either substrate. The term "shaped" means that at least one end region of the absorbent core 14 has an average width (in the lateral direction) which is greater than the average width in the central region. The average width in the at least one end region may be at least 5% greater, or at least 10% greater, or at least 25% greater, or at least 50% greater than the average width in the central region. Both end regions may have an average width which is at least 5% greater, or at least 10% greater, or at least 25% greater, or at least 50% greater than the average width of central region. For further disclosure regarding shaped cores, see U.S. Pat. No. 7,938,813, which is incorporated herein by reference.

Figure 4:
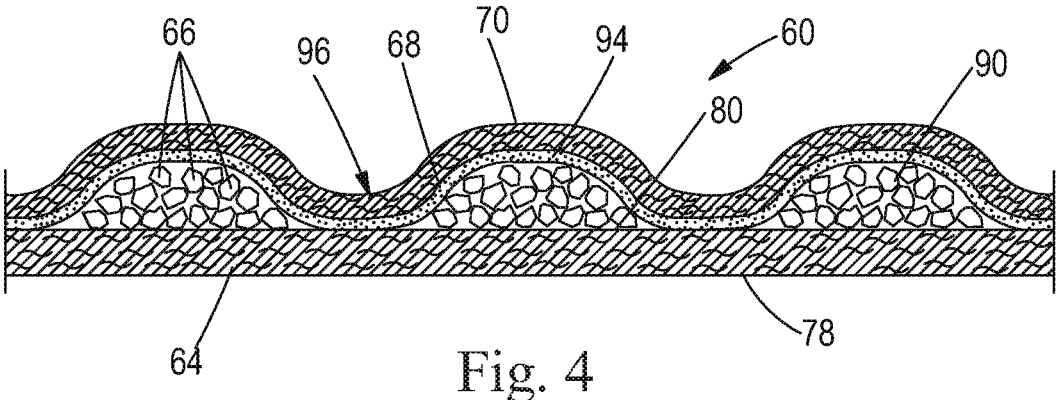
FIG. 4 is a partial cross sectional view of an exemplary absorbent core layer in accordance with the absorbent article described herein.
Figure 5:
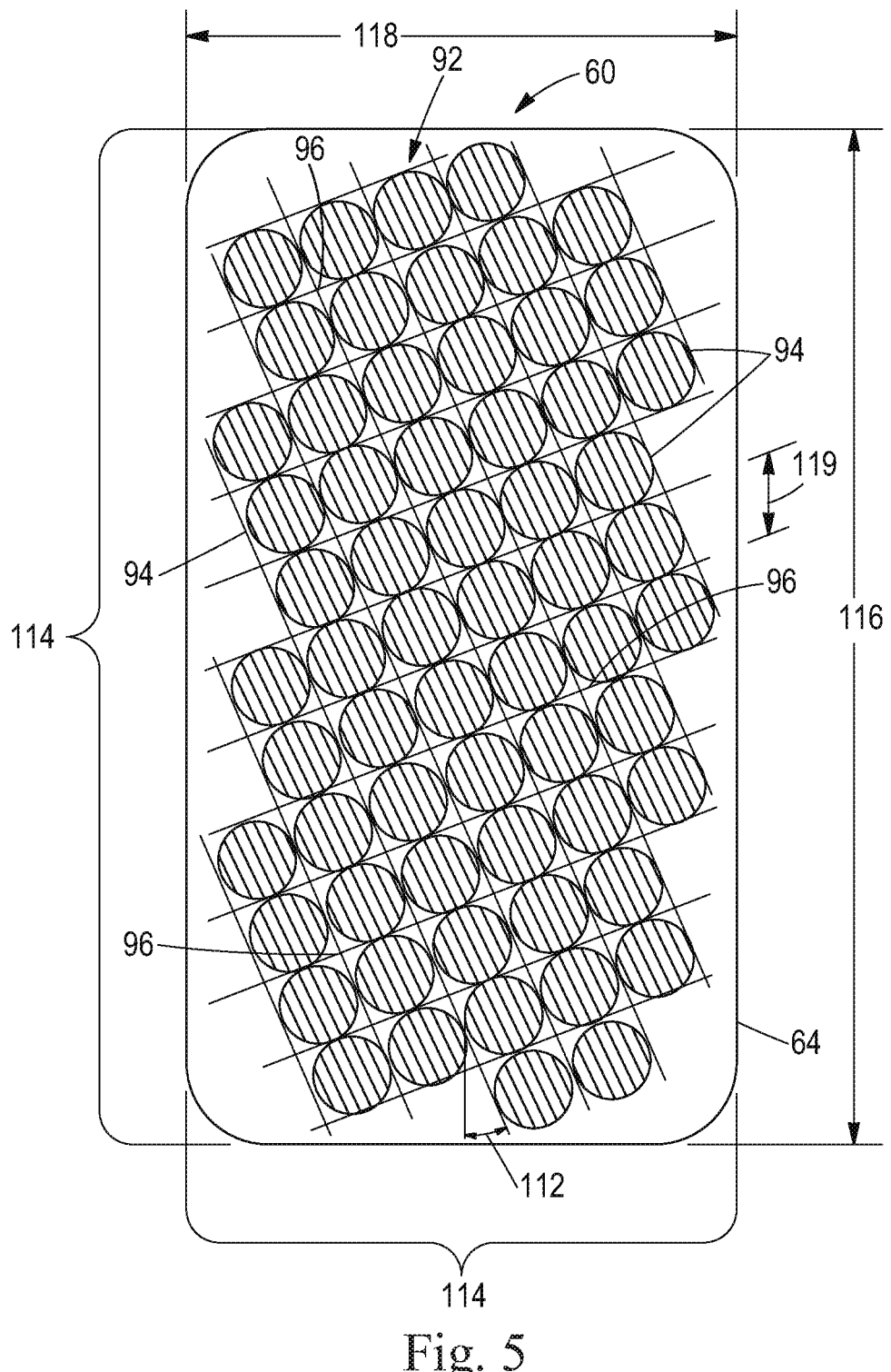
FIG. 5 is a plan view of the absorbent core layer illustrated in FIG. 3.
Figure 6:
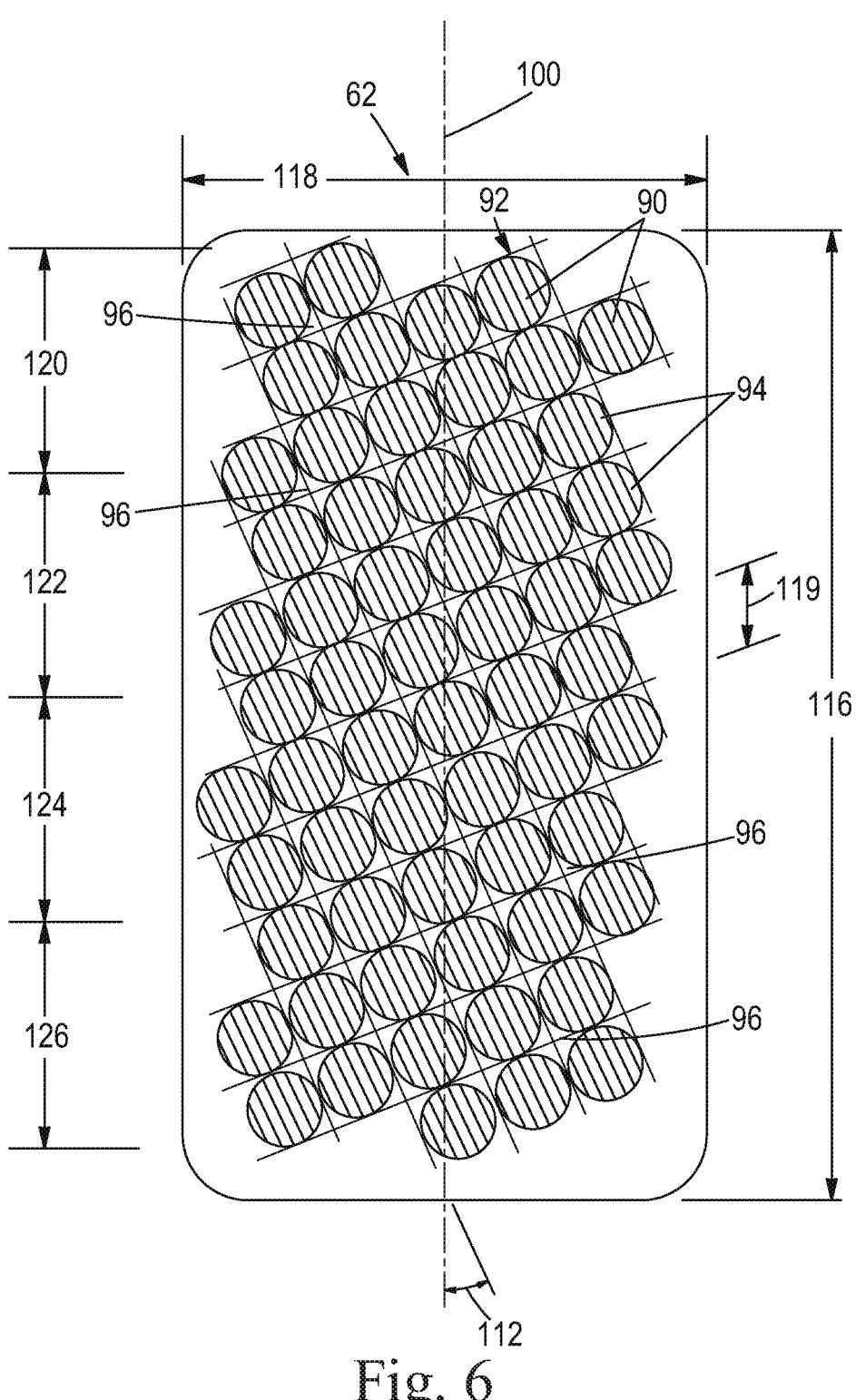
FIG. 6 is a plan view of a second exemplary absorbent core layer in accordance with the absorbent article described herein.

The superabsorbent polymer immobilizing material, SPIM, 68 and 76 may serve to cover and at least partially immobilize the superabsorbent particulate polymer material 66 and 74. The SPIM 68 and 76 can be disposed essentially uniformly within the superabsorbent particulate polymer material 66 and 74, between the particles of the superabsorbent absorbent material. However, the SPIM 68 and 76 may be provided as a fibrous layer which is at least partially in contact with the superabsorbent particulate polymer material 66 and 74 and partially in contact with the substrate layers 64 and 72 of the first and second absorbent layers 60 and 62. FIGS. 3, 4, and 7 show such a structure, and in that structure, the superabsorbent particulate polymer material 66 and 74 is provided as a discontinuous layer, and a layer of a fibrous thermoplastic composition or fiberized structure 68 and 76 is laid down onto the layer of superabsorbent particulate polymer material 66 and 74, such that the fiberized structure 68 and 76 is in direct contact with the superabsorbent particulate polymer material 66 and 74, but also in direct contact with the second surfaces 80 and 84 of the substrates 64 and 72, where the substrates are not covered by the superabsorbent particulate polymer material 66 and 74. The fiberized structures of each substrate, 68 and 76, may essentially be one fiberized structure, each contacting the other. This imparts an essentially three-dimensional structure to the fibrous structure of thermoplastic composition 68 and 76, which in itself is essentially a two-dimensional structure of relatively small thickness, as compared to the dimension in length and width directions. In other words, the thermoplastic composition 68 and 76 undulates between the superabsorbent particulate polymer material 66 and 74 and the second surfaces of the substrates 64 and 72, forming a fiberized structure 68 and 76.

The SPIM 68 and 76 may provide cavities to cover the superabsorbent particulate polymer material 66 and 74, and thereby immobilize the material. The SPIM 68 and 76 may immobilize the superabsorbent particulate polymer material 66 and 74 when wet. Some SPIM may also penetrate into both the layers of superabsorbent particulate polymer material 66 and 74 and into the substrates 64 and 72, thus providing for further immobilization. Of course, while the SPIM disclosed herein provide a much improved wet immobilization (i.e., immobilization of superabsorbent polymer material when the absorbent article is wet or at least partially loaded), these SPIM may also provide a very good immobilization of superabsorbent polymer material when the absorbent core 14 is dry. The SPIM may be a fiberized structure, a film, nanofibers, irregular blobs of material, and/or other forms.

The SPIM may function as a fibrous structure that entraps the superabsorbent particulate polymer 66 and prevents substantial movement. Materials that are most useful as a superabsorbent polymer immobilizing material include polymers with good cohesion and good elasticity or flexibility to reduce the likelihood that the superabsorbent polymer immobilizing material breaks in response to strain. In addition, the superabsorbent particulate polymer material will swell when wet, requiring the superabsorbent polymer immobilizing material to allow for such swelling without breaking and without imparting too many compressive forces, which would restrain the superabsorbent particulate polymer material from swelling. Elasticity and flexibility in the SPIM also promotes overall article flexibility and its ability to conform to the wearer. Overall, flexible polymers having low storage modulus, i.e., G' (as discussed later) may be used in the SPIM. Without being bound by theory, semicrystalline polymers that have low storage modulus can also have low amounts of crystallinity. These low-crystallinity, low storage modulus polymers have an amorphous phase (defined as the remaining volume of the polymer that is not crystalline) that is elastic and rubbery at the desired temperature. A practical means to determine a polymer's level of crystallinity is by measuring its heat of fusion (melting). Polymers that have high heats of fusion are more crystalline than those that do not, so polymers with low heats of fusion may be used for the superabsorbent polymer immobilizing material. In addition, the amorphous portion of a low-crystallinity semicrystalline polymer has greater integrity and cohesion when its molecular weight is higher and thus preserves the superabsorbent polymer immobilizing material's mechanical integrity during extension. For a superabsorbent polymer immobilizing material, polymers with relatively high molecular weight may be used.

The absorbent core 14 may also comprise an auxiliary adhesive which is not illustrated in all the figures. The auxiliary adhesive may be deposited on the first and second substrates 64 and 72 of the respective first and second absorbent layers 60 and 62 before application of the superabsorbent particulate polymer material 66 and 74 for enhancing adhesion of the superabsorbent particulate polymer materials 66 and 74 and the SPIM 68 and 76 to the respective substrates 64 and 72. The auxiliary adhesive may be deposited on a nonwoven that is the most hydrophilic for improved bonding. The auxiliary glue may also aid in immobilizing the superabsorbent particulate polymer material 66 and 74. The auxiliary glue may be applied to the substrates 64 and 72 by any suitable means, but may be applied in about 0.5 mm to about 1 mm wide slots spaced about 0.5 mm to about 2 mm apart. Exemplary auxiliary adhesives include, but are not limited to, sprayable hot melt adhesives, such as H.B. Fuller Co. (St. Paul, MN) Product No. HL-1620-B. Other suitable auxiliary adhesives may include low-tackifier or tackifier-free adhesives such as those disclosed in U.S. Ser. No. 62/267,536, which is hereby incorporated by reference. One thermoplastic composition may be used to provide immobilization of the superabsorbent particulate polymer, while an auxiliary adhesive is used in conjunction with the thermoplastic composition to adhere materials in other areas in the core. A SPIM material may be used as an auxiliary adhesive in the core.

The SPIM and/or auxiliary adhesive may be applied in the superabsorbent particulate polymer material area at a basis weight of from about 2 grams/meter 2 to about 7 grams/meter 2 (gsm) or from about 5 gsm to about 15 gsm. This may be a combined basis weight from application on a first and a second substrate, for example, 4 gsm and 3 gsm, respectively. The auxiliary adhesive may be applied in the superabsorbent particulate polymer material area in any amount from about 0 gsm to about 8 gsm, about 5 gsm, or about 8 gsm. The total amount of adhesive and SPIM may be from about 2 gsm to about 15 gsm in the superabsorbent particulate polymer material area. The front end seal may have from about 10 gsm to about 35 gsm of adhesive. Similarly, the back end seal may have from about 10 gsm to about 35 gsm of adhesive. Either or both of the front and back end seals may have from about 5 gsm to 15 gsm of adhesive. The amount of adhesive in an end seal may be a combination of the auxiliary adhesive and the end seal adhesive.

The SPIM 68 and 76 may be present in the form of fibers. The fiberized structure may have a range of thickness from about 1 micrometers to about 90 micrometers, from about 1 micrometers to about 50 micrometers, or from about 1 micrometers to about 35 micrometers, and an average length of about 0.1 mm to about 5 mm or about 0.5 mm to about 6 mm. The average fiber thickness may be about 30 micrometers, or may be from about 20 micrometers to about 45 micrometers. Substrates 64 and 72, or any nonwoven layer, may be pre-treated with an auxiliary adhesive.

The fiberized structure may consist of continuous extruded polymer strands, which create a net structure with irregular strand or filament thickness or with irregular open areas (pores or maximum strand to strand distance). Continuous polymer strands may overlap and form strand crossings or overlaps with different diameters. The applied fiberized structure may build a three-dimensional net in the absorbent core as described herein. At equivalent basis weights, a fiberized structure with thicker fibers may be more open and irregular than a fiberized structure with thinner fibers. It is believed that the thicker fibers can maintain heat in the fiber longer, which can allow the fiberized structure to wet and penetrate a nonwoven better, allowing for better stability.

If, for example, the core has channels (as discussed below) and the channels are then more secure, that is, are permanent channels, the more open structure of the fiberized structure allows the AGM or superabsorbent polymer material to adjust or move within its confined area. An exemplary SPIM 68 and 76, as described in more detail below, may have a storage modulus G' measured at 25° C. of less than $1.2 \times 10^9$ Pa as measured by the test method described herein. The compositions described herein may have high G' values, but may still be not too stiff to work as a SPIM or a fiberized structure in absorbent articles. A composition with a relatively high G', such as greater than $1.2 \times 10^6$ Pa, means a stiffer composition. It is believed that such a composition can promote thicker microfibers, and that this can aid in providing better dry superabsorbent polymer material stability. The net structure formed by the strands or fibers of the SPIM may be less dense, thus providing more volume at the same basis weight. This is particularly true for fiberized structures comprising polyolefins.

When the absorbent article contains channels, the SPIM may not only help in immobilizing the absorbent material on the substrate, but it may also help in maintaining the integrity of the channels in the absorbent structure absorbent core during storage and/or during use of the disposable article. The SPIM may help to avoid that a significant amount of absorbent material migrates into the channels. Furthermore, when the materials are applied in the channels or on the substrate portions coinciding with the channels it may thereby help to hold the substrate of the absorbent structure to said walls, and/or to a further material, as will be described in further details below. A SPIM may be applied as fibers, forming a fibrous network that immobilizes the absorbent material on the substrates. The thermoplastic fibers may be partially in contact with the substrate of the absorbent structure; if applied also in the channels, it (further) anchors the absorbent layer to the substrate. The thermoplastic composition material may allow for such swelling without breaking and without imparting too many compressive forces, which would restrain the superabsorbent polymer particles from swelling.

The cover layer 70 shown in FIG. 4 may comprise the same material as the substrates 64 and 72, or may comprise a different material. Suitable materials for the cover layer 70 may be nonwoven materials, typically the materials described above as useful for the substrates 64 and 72. The nonwovens may be hydrophilic and/or hydrophobic.

Figure 9:
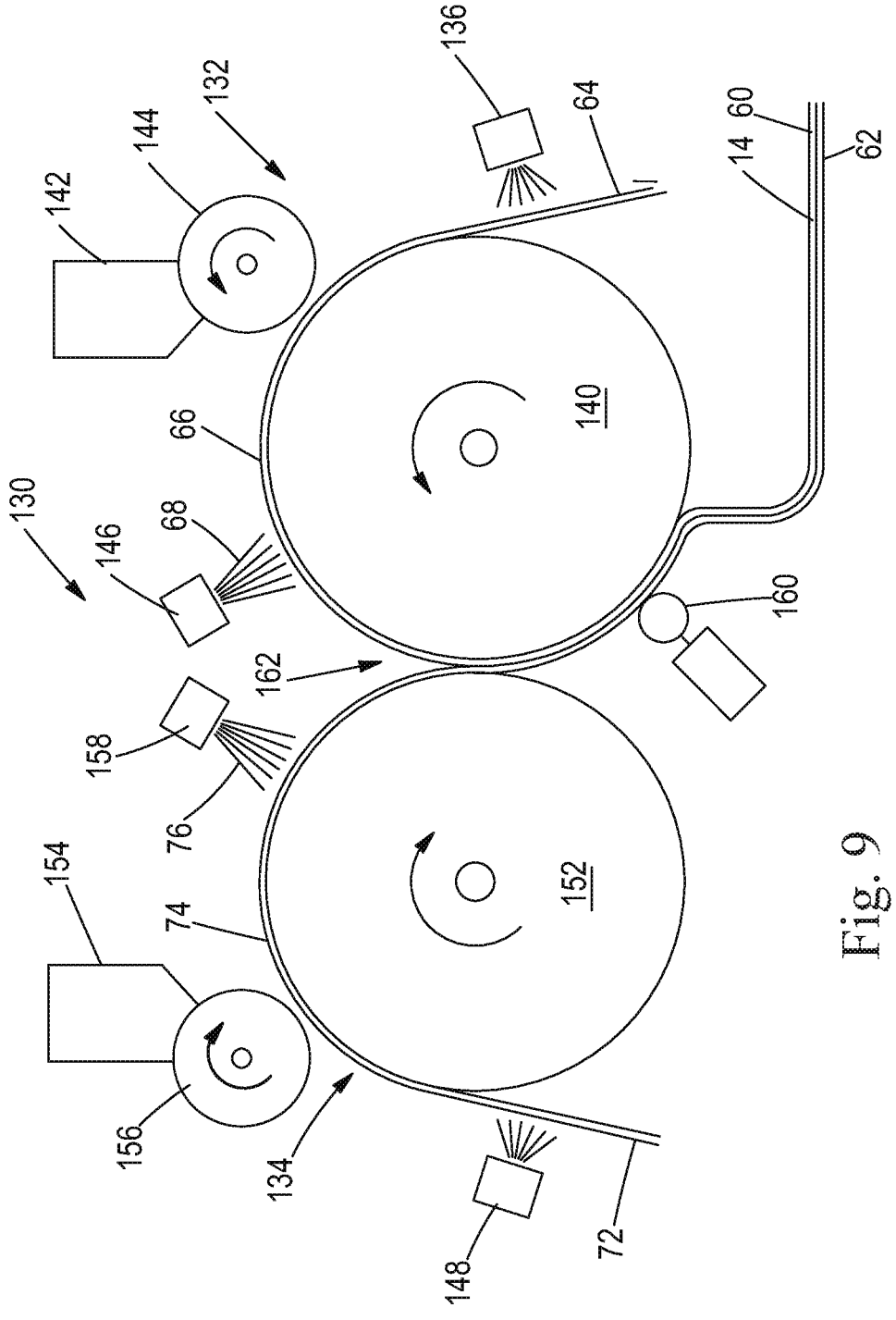
FIG. 9 is a schematic illustration of an exemplary process for making an absorbent core in accordance with the absorbent article described herein.

A printing system 130 for making an absorbent core 14 as described herein is illustrated in FIG. 9 and may generally comprise a first printing unit 132 for forming the first absorbent layer 60 of the absorbent core 14 and a second printing unit 134 for forming the second absorbent layer 62 of the absorbent core 14.

The first printing unit 132 may comprise a first auxiliary adhesive applicator 136 for applying an auxiliary adhesive to the substrate 64, which may be a nonwoven web, a first rotatable support roll 140 for receiving the substrate 64, a hopper 142 for holding superabsorbent particulate polymer material 66, a printing roll 144 for transferring the superabsorbent particulate polymer material 66 to the substrate 64, and a SPIM applicator 146 for applying the SPIM 68 to the substrate 64 and the superabsorbent particulate polymer 66 material thereon.

The second printing unit 134 may comprise a second auxiliary adhesive applicator 148 for applying an auxiliary adhesive to the second substrate 72, a second rotatable support roll 152 for receiving the second substrate 72, a second hopper 154 for holding the superabsorbent particulate polymer material 74, a second printing roll 156 for transferring the superabsorbent particulate polymer material 74 from the hopper 154 to the second substrate 72, and a second SPIM applicator 158 for applying the SPIM 76 to the second substrate 72 and the superabsorbent particulate polymer material 74 thereon.

The printing system 130 also includes a guide roller 160 for guiding the formed absorbent core from a nip 162 between the first and second rotatable support rolls 140 and 152.

The first and second auxiliary applicators 136 and 148 and the first and second SPIM applicators 146 and 158 may be a nozzle system which can provide a relatively thin but wide curtain of SPIM. A contact application such as a slot gun may be used.

The absorbent article may further comprise a wetness indicator which is visible from the exterior of the article and which changes appearance when contacted with a body exudates, in particular urine. The wetness indicator (not shown) may be placed, when seen from the exterior of the article, between the two channel-forming areas 226a,b, of FIG. 10, and/or between any of the channel-forming areas 226a, 226b and any of the lateral edge or both. The wetness indicators may be according to any wetness indicating system known in the art. It is known that wetness indicator can provide an appearing signal, a disappearing signal or a color change signal, and combinations thereof. The wetness indicator may advantageously provide a color change signal, which may be typically obtained by a composition having a first color when dry and a second color different form the first color when wet, both colors being discernible by an external observer considering the article in a dry and a wet state.

The wetness indicator may in particular be a color change composition comprising a suitable pH indicator or another chemical substance that changes color when contacted with urine. Such compositions are for example disclosed in WO03/070138A2 or US2012/165771 (Ruman), which are incorporated herein by reference. More generally, the wetness indicator compositions may be chosen from those disclosed in WO2010/120705 (Klofta), which is incorporated herein by reference, comprising a colorant, a matrix and a stabilizer. The color change composition may be a hot-melt adhesive, which allows for an easy application of the composition on a substrate component of the article for example by a slot coating process or printed adhesive coating as disclosed e.g. in US2011274834 (Brown), which is incorporated herein by reference. The wetness indicator composition may be applied on any layer of the absorbent article using a conventional technique, for example printing, spraying or coating, during the making of the absorbent article. The layer may advantageously be the inner surface of the backsheet or the outer surface of the bottom side of the core wrap. This allows the wetness indicator to be visible from the exterior of the article by transparency through the backsheet while keeping the wetness indicator composition within the article. The wetness indicator may in particular be easily applied on a layer such a nonwoven or film by a slot-coating process especially if the composition is can be applied as a hot-melt.

Channels

The absorbent core and/or the superabsorbent polymer material area 114 may comprise channels, or areas substantially free of superabsorbent polymer particles or any absorbent polymer material. The channels may provide improved liquid transport, and hence faster acquisition, and more efficient liquid absorbency over the whole absorbent structure, in addition to reducing the stiffness of partially or fully loaded cores.

Figure 10:
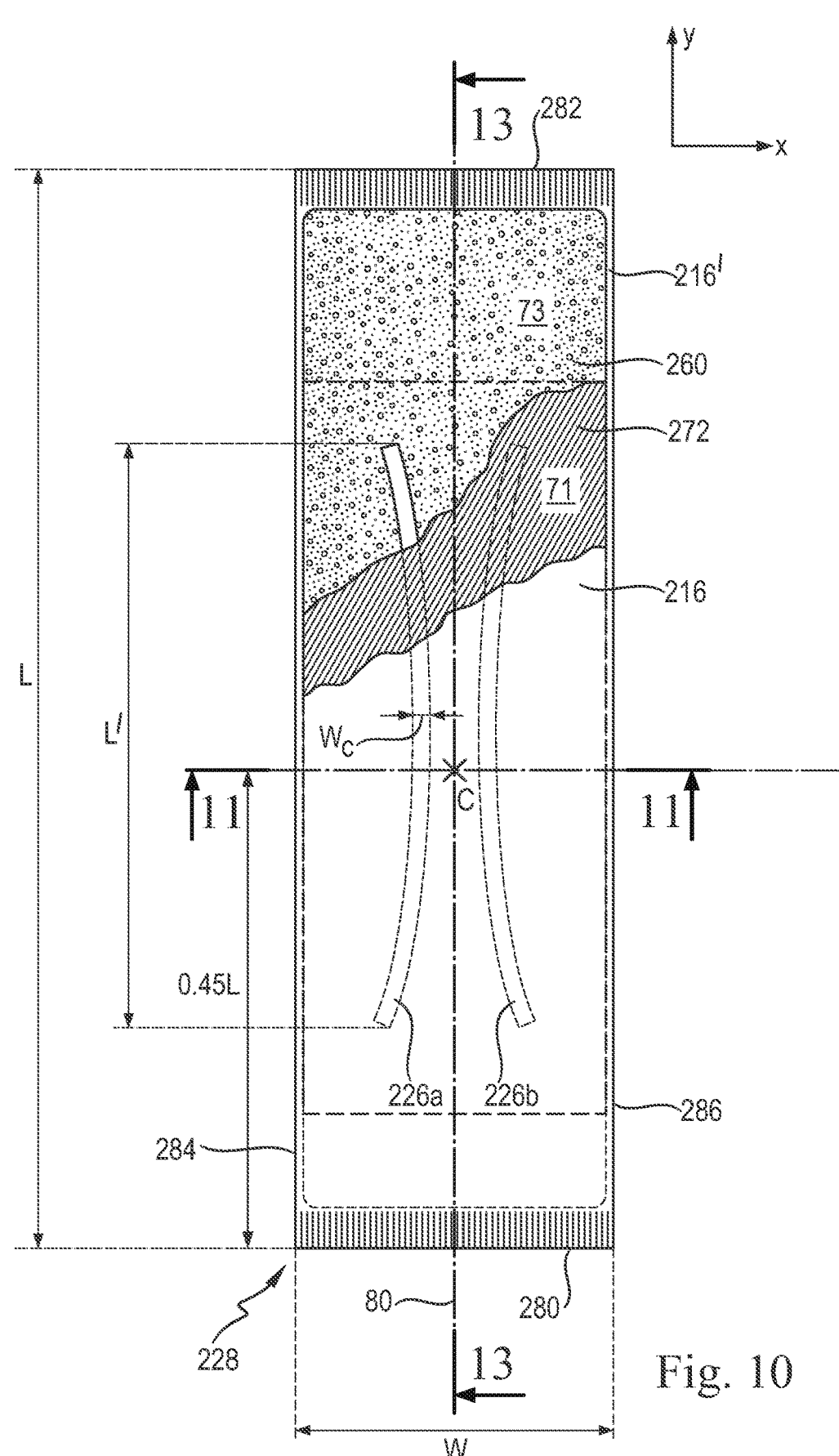
FIG. 10 is a top view of an exemplary absorbent core according to the absorbent article described herein with some of the layers partially removed.

In FIG. 10-14, an exemplary absorbent core comprises a front side 280, a back side 282 and two longitudinally extending lateral sides 284, 286 joining the front side 280 and the back side 282. The absorbent core also comprises a generally planar top side 288 and a generally planar bottom side 290 formed by the core wrap. Referring to FIG. 10, the absorbent material deposition area 73 of the core (also referred to as the superabsorbent polymer material area 114 of earlier figures) encompasses one or more area(s) 226 (e.g., 226a and 226b) which is/are substantially free of absorbent material. By "substantially free" it is meant that in each of these areas the basis weight of the absorbent material is less than 25%, alternatively less than 20%, and alternatively less than 10% of the average basis weight of the absorbent material in the rest of the absorbent material deposition area 73 of the core. In particular there can be no absorbent material in these areas 226a and 226b. Minimal amount such as involuntary contaminations with absorbent material particles that may occur during the making process are not considered as absorbent material. The areas 226 are advantageously surrounded by the absorbent material, when considering the plane of the core, which means that the area(s) 226 does not extend to any of the edges of the deposition area 73 of the absorbent material.

Figure 12:
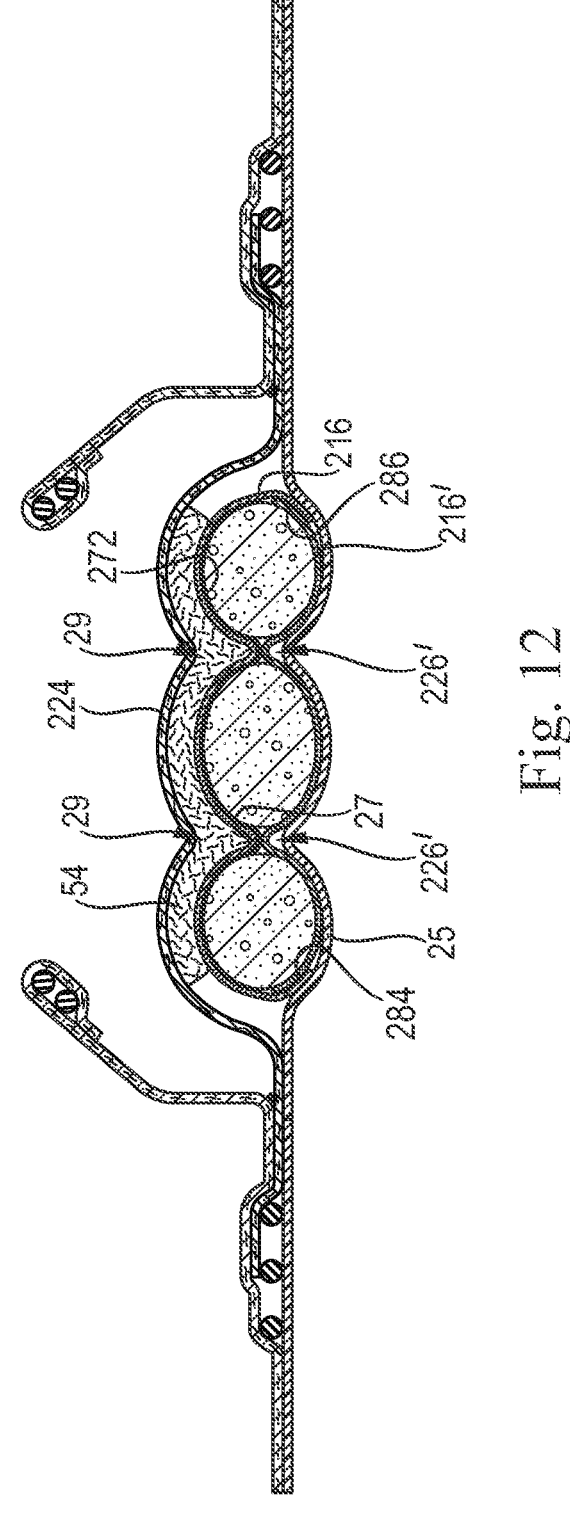
FIG. 12 shows a transversal cross-section of the article of FIG. 10 along 2-2 when the absorbent core has swollen after absorbing a fluid.

As shown for example in FIG. 11, the top side 216 of the core wrap is attached to the bottom side 216' of the core wrap by at least one core wrap bond(s) 27 through these area(s) 226 substantially free of absorbent material. As illustrated in FIGS. 11 and 12, when the absorbent material 260 swells upon absorbing a liquid, the core wrap bond(s) 27 remain(s) at least initially attached in the substantially absorbent material-free area(s) 226. The absorbent material 260 swells in the rest of the core when it absorbs a liquid, so that the core wrap forms one or more channel(s) 226' along the area(s) 226 substantially free of absorbent material comprising the core wrap bond 27. These channels 226' are three dimensional and can serve to distribute an insulting fluid along their length to a wider area of the core. They may provide a quicker fluid acquisition speed and a better utilization of the absorbent capacity of the core. The channels 226' can also provide a deformation of an overlying layer such as fibrous layer 54 and provide corresponding ditches 29 in the overlying layer. It is not excluded that the absorbent core may comprise other area(s) substantially free of absorbent material but without a core wrap bond, but these non-bonded areas will typically not form a channel when wet.

The inner surface of the first substrate 216 and the inner surface of the second substrate 216' may be attached together continuously along the area(s) 226 substantially free of absorbent material, but the core wrap bond 27 may also be discontinuous (intermittent) such as formed by series of point bonds. The auxiliary glue at least partially helps forming the substrates bond 27. Typically, some pressure may be applied on the substrates in the areas 26 so that the auxiliary glue may better attach to and from the bonds between the substrates. It is also possible to additionally form the bond via other known attachment means, such as pressure bonding, ultrasonic bonding or heat bonding or combination thereof. If the auxiliary glue is applied as a series of continuous slots 272s, the width and frequency of these slots may advantageously be such that at least one slot of auxiliary glue is present at any level of the channel in the longitudinal direction. For example, the slots may be 1 mm wide with a 1 mm distance between each slot, and the channel-forming area(s) have a width of about 8 mm. Such on average for 4 slots of auxiliary glue will be present in area(s) 226.

The following examples of the shape and size of the channel-forming areas 226 substantially free of absorbent material are not limiting. In general, the core wrap bond 27 may have the same outline but be slightly smaller than the areas 226 due to the tolerance required in some manufacturing process. The substantially absorbent material free area(s) 226 may be present within the crotch region of the core, in particular at least at the same longitudinal level as the crotch point C, as represented in FIG. 10 by the two longitudinally extending areas substantially free of absorbent material 226a, 226b. The absorbent core 228 may also comprise more than two substantially absorbent material free area(s), for example at least 3, or at least 4 or at least 5 or at least 6. The absorbent core may comprise one or more pairs of areas 226a, 226b substantially free of absorbent material symmetrically arranged relative to the longitudinal axis 80. Shorter area(s) substantially free of absorbent material may also be present, for example in the back region or the front region of the core, as seen for example in the Figures of WO2012/170778, which is incorporated herein by reference.

The channel-forming area(s) 226 may extend substantially longitudinally, which means typically that each area extends at least as much in the longitudinal direction (y) than in the transversal direction (x), and typically at least twice as much in the longitudinal direction than in the transverse direction (as measured after projection on the respective axis). The area(s) 226 substantially free of absorbent material may have a length L' projected on the longitudinal axis 80 of the core that is at least 10% of the length L of the absorbent core, alternatively from about 20% to about 80%. It may be advantageous that at least some or all of the channel-forming area(s) 226 are not completely or substantially completely transversely oriented. The area(s) substantially free of absorbent material may have a width Wc along at least part of its length which is at least 2 mm, or at least 3 mm, or at least 4 mm, up to, for example, 20 mm, or 16 mm or 12 mm. The width Wc of the area(s) substantially free of absorbent material may be constant through substantially its whole length or may vary along its length.

The area(s) 226 substantially free of absorbent material may be completely oriented longitudinally and parallel to the longitudinal axis but also may be curved. In particular some or all these area(s), in particular these area(s) present in the crotch region, may be concave towards the longitudinal axis 80, as for example represented in FIG. 10 for the pair of channels 226a,b. The radius of curvature may typically be at least equal (or at least 1.5 or at least 2.0 times this average transverse dimension) to the average transverse dimension of the absorbent material deposition area 73; and also straight but under an angle of (e.g. from 5°) up to 30°, or for example up to 20°, or up to 10° with a line parallel to the longitudinal axis. The radius of curvature may be constant for a substantially absorbent material free area(s), or may vary along its length. This may also includes area(s) substantially free of absorbent material with an angle therein, provided said angle between two parts of a channel is at least 120°, alternatively at least 150°; and in any of these cases, provided the longitudinal extension of the area is more than the transverse extension. These area(s) may also be branched, for example a central substantially material free area superposed with the longitudinal axis in the crotch region which branches towards the back and/or towards the front of the article.

There is no area(s) substantially free of absorbent material that coincides with the longitudinal axis 80 of the core. When present as one or more symmetrical pair(s) relative to the longitudinal axis, the area(s) substantially free of absorbent material may be spaced apart from one another over their whole longitudinal dimension. The smallest spacing distance may be for example at least 5 mm, or at least 10 mm, or at least 16 mm.

Furthermore, in order to reduce the risk of fluid leakages, the area(s) substantially free of absorbent material may advantageously not extend up to any of the edges of the absorbent material deposition area 73, and are therefore surrounded by and fully encompassed within the absorbent material deposition area 73 of the core. Typically, the smallest distance between an area(s) substantially free of absorbent material and the closest edge of the absorbent material deposition area is at least 5 mm.

The channels 226' in the absorbent core start forming when the absorbent material absorbs a liquid such as urine and starts swelling. As the core absorbs more liquid, the depressions within the absorbent core formed by core wrap bond 27 between the two substrates will become deeper and more apparent to the eye and the touch. It is possible to create a sufficiently strong core wrap bond combined with a relatively low amount of superabsorbent polymer material and/or a relatively extensible substrate material so that the channels remain permanent until complete saturation of the absorbent material. On the other hand, the core wrap bonds may in some cases also restrict the swelling of the absorbent material when the core is substantially loaded. The core wrap bond 27 may also be designed to gradually open in a controlled manner when exposed to a large amount of fluid. The bonds may thus remain substantially intact at least during a first phase as the absorbent material absorbs a moderate quantity of fluid, as shown on FIG. 11. In a second phase the core wrap bonds 27 in the channels can start opening to provide more space for the absorbent material to swell while keeping most of the benefits of the channels such as increased flexibility of the core in transversal direction and fluid management. In a third phase, corresponding to a very high saturation of the absorbent core, a more substantial part of the channel bonds can open to provide even more space for the swelling absorbent material to expand. The strength of core wrap bond 27 within the channels can be controlled for example by varying the amount and nature of the bond used for the attaching the two sides of the core wrap, the pressure used to make the core wrap bond and/or the distribution of the absorbent material, as more absorbent material will usually causes more swelling and will put more pressure on the bond. The extensibility of the material of the core wrap may also play a role.

As shown in FIGS. 10-14, an auxiliary glue 272 is applied directly over the substrate 216 on an auxiliary glue application area 71. The auxiliary glue at least partially forms the bonds 27 between the inner surface of the first substrate 216 and the inner surface of the second substrate 216' through the area(s) 226a,b substantially free of absorbent material. The auxiliary glue 272 may also be useful to improve the adhesion between the first substrate 216 and both the absorbent material (in the absorbent material land areas 75) and the SPIM 274 (in the absorbent material-free junction areas 276).

The "auxiliary glue application area" as used herein means the smallest area 71 in the plane of the substrate 216 whose periphery encompasses the auxiliary glue 272 and any areas free of auxiliary glue between the auxiliary glue. The auxiliary glue application area 71 is smaller than the absorbent material deposition area 73 (superabsorbent polymer material area). The auxiliary glue may thus be applied in the area of the first substrate 216 where it is most needed, foremost where the channel-forming region(s) 226a,b are present and a bond 27 between the two substrates is desired, and typically at or close to the crotch region of the absorbent core as well where the amount of absorbent material may be typically higher than in the back region of the core. Reducing the auxiliary glue application area 71 relative to the absorbent material deposition area 73 has the advantage that typically less auxiliary glue material is used compared to a full application area. Reducing the amount and area of the auxiliary glue may also provide improved fluid acquisition properties as hotmelt glue are typically hydrophobic as well as reduced undesired glue smell in the finished product.

In general, the auxiliary glue application area may be at least 20% smaller than the absorbent material deposition area 73, in particular from 20% to 80% smaller than the absorbent material deposition area 73. The areas are compared by measuring their surface in the plane of the absorbent core and including the channel-forming area 226' in the absorbent material deposition area 73.

The auxiliary glue application area may be shorter in the longitudinal direction (y) and/or in the transversal direction (x) than the absorbent material deposition area 73. The auxiliary glue application area 71 may be for example generally rectangular and have about the same width as the absorbent material deposition area 73 while being shorter in the longitudinal direction (y). FIG. 10 shows such an example where the auxiliary glue application area 71 and absorbent material deposition area 73 are both rectangular, have the about the same width and wherein the application area 71 is longitudinally shorter than the deposition area 73 and does not extend to any of the front or back ends of the absorbent material deposition area. An alternative configuration may be where the auxiliary glue application area 71 is shorter in both longitudinal and transversal directions than the absorbent material deposition area 73. Of course, many different configurations for the both areas are possible, as the absorbent material deposition area 73 may also be shaped instead of rectangular. The auxiliary glue application area 71 may also for example extend from the front end of the absorbent material deposition area 73 and along its width and stop before the back end of the absorbent material deposition area. This may be advantageous for application having a relatively high amount of superabsorbent polymer material towards the front of the core, where the auxiliary glue may be needed there. The auxiliary glue application area may also have a shape which is not rectangular but for example having a central body with two adjoined side wings which are shorter than the central body. The wings may or may not extend to the lateral edges of the absorbent material deposition area but they may also extend to these edges if desired. These sections of different lengths may for example be easily obtained using a slot coating process and tuning the slot nozzles to apply the hot-melt adhesive on a shorter distance on the sides of the application area compared to the center of the application area.

The auxiliary glue application area 71 may have any shape adapted to the intended usage of the absorbent article and the distribution of absorbent material. In particular, the auxiliary glue application area may be rectangular, shaped with a tapering in the central region of the substrate, or with a central elongated portion and shorter side portions. It is also possible that the auxiliary glue application area comprises separated sub-areas. A sub-area is hereby defined as an adhesive application area separated from another at least 10 mm. In that case the adhesive free area between the adhesive application sub-areas is not considered to be part of the auxiliary glue application area, for example for the determination of the surface of the auxiliary glue area 71. In such a configuration, where the auxiliary glue application area 71 consists of two sub-zones, each of these zones generally corresponding to one channel-forming area 226a, 226b and separated by a distance of about 10 mm.

In the above description, the auxiliary glue 272 was discussed with reference to the first absorbent substrate 216 which forms the upper side 288 of the absorbent core, and which is placed towards the topsheet 224 in the finished absorbent article 20. This is however not limiting, as the first substrate may alternatively form the bottom side 290 of the absorbent core which is placed towards the backsheet 25 of the article 20. It is also considered that a second auxiliary glue may be applied directly on the second substrate in addition to the first auxiliary glue applied directly on the first substrate, in particular in any of the configurations discussed above. This may be particular useful when the absorbent material within the core wrap comprises two layers as discussed above.

Figures 13, 14:
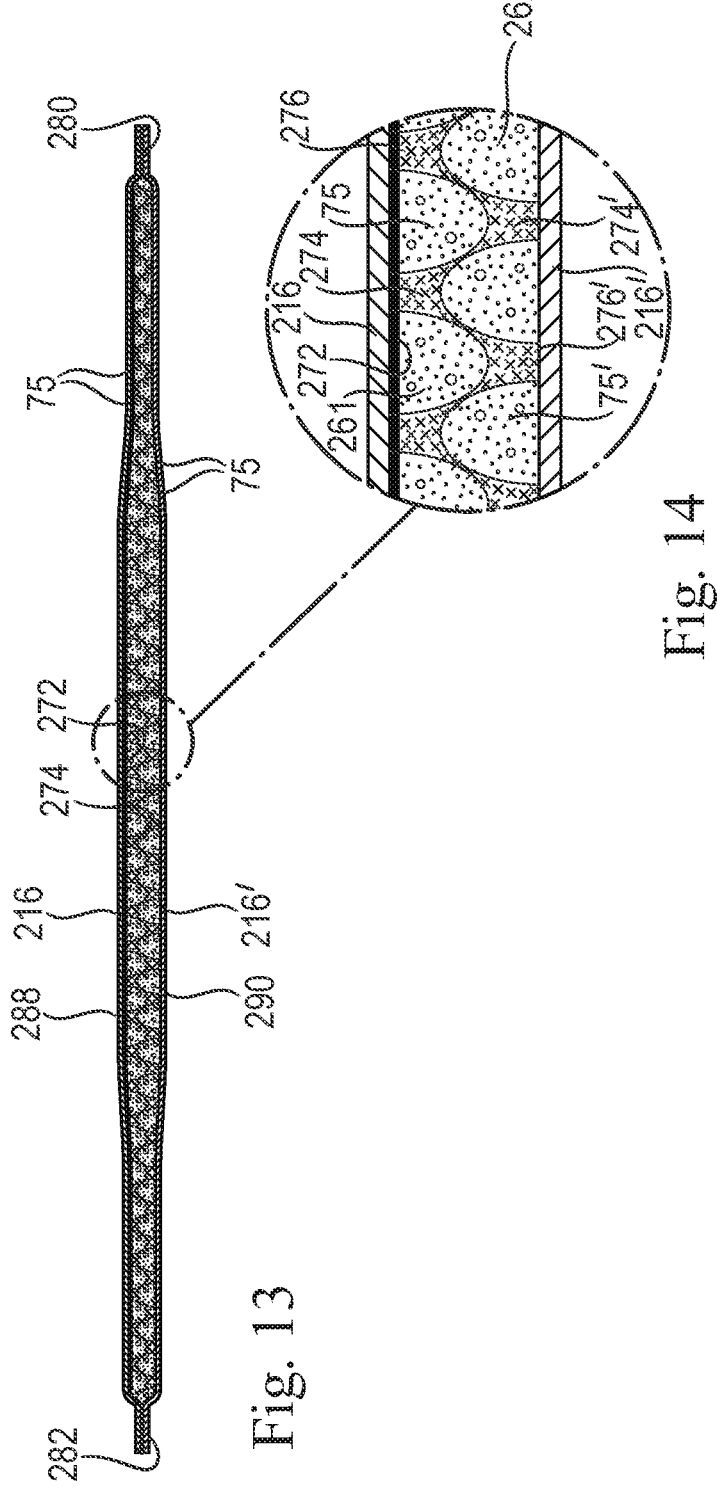
FIG. 13 is the longitudinal cross-section of the core of FIG. 10 along 3-3, showing an optional dual layer construction for the absorbent layer.
FIG. 14 is a close-up view of a section of FIG. 13.

As shown in FIGS. 13 and 14, the absorbent core may also comprise a superabsorbent polymer immobilizing material (SPIM) 274, which may be a fibrous thermoplastic material, to further immobilize the absorbent material 261 and 262 during the making process of the core and usage of the article. This SPIM 274, 274' may be in particular useful to immobilize the layer of absorbent materials 261, 262 to their respective substrate 216, 216'. These absorbent layer(s) may comprise land areas 75, 75' separated by junction areas 276, 276' as discussed above and the SPIM 274 may then be at least partially in contact with the absorbent material 261, 262 in the land areas and at least partially in contact with the substrate layer 216, 216' in the junction areas. This imparts an essentially three-dimensional net-like structure to the SPIM, which in itself may be essentially a two-dimensional structure of relatively small thickness, as compared to the dimension in length and width directions. Thereby, the SPIM may provide cavities to cover the absorbent material in the land areas, and thereby immobilizes this absorbent material. The SPIM may be for example sprayed on an absorbent layer after it has been deposited on its substrate during the core making process.

Superabsorbent Polymer Immobilizing Material ("SPIM")

The SPIM is a composition that is applied to the super-absorbent polymer material with the intent to immobilize the superabsorbent polymer material in both the dry and wet state. The SPIM may be a fiberized structure with, for example, microfibers or nanofibers, or may be a film, or discrete blobs of material, or some other form. The SPIM may be, for example, a discrete form such as a layer of material, or a fiberized net structure that interweaves or intertwines with surrounding materials, such as the particles of superabsorbent polymer material. A single absorbent core may have more than one SPIM, if the SPIM is in a countable form such as discrete layers. A single absorbent core may have more than one area comprising SPIM, and some of the SPIM from each area may or may not have contact or intertwine. A single absorbent core may have more than one form of SPIM.

The SPIM described herein comprises a first polymer and a second polymer wherein the first polymer is selected from the class of random and/or block copolymers having ethyl-ene derived units and/or C3-C10 alpha olefin derived units (herein denoted as "class 1"), or from the class of poly-olefinic homopolymers having ethylene derived units or propylene derived units or 1-butene derived units ("class 2"), or from the class of styrenic block copolymers ("class 3"), or a blend or mixture of polymers selected from any of the three classes, and wherein the second polymer is a polyolefin.

In the case that the first polymer belongs to class 1 or class 2, its peak molecular weight, as determined using the Peak Molecular Weight Test Method described herein, may be from about 70,000 g/mol to about 700,000 g/mol, alterna-tively from about 75,000 g/mol to about 500,000 g/mol, and alternatively from about 100,000 g/mol to about 310,000 g/mol. In the case that the first polymer belongs to class 3, its peak molecular weight may be from about 20,000 g/mol to about 150,000 g/mol, alternatively from about 30,000 g/mol to about 110,000 g/mol.

The peak molecular weight of the second polymer, as determined using the Peak Molecular Weight Test Method described herein, may be from about 1,000 g/mol to about 90,000 g/mol, alternatively from about 15,000 g/mol to about 60,000 g/mol, and alternatively from about 30,000 to about 60,000 g/mol.

The first polymer may have a fusion index from about 0% to about 15%, as measured using the Fusion Index Test Method described herein, and a glass transition temperature of below 0° C., as measured using the Glass Transition Temperature Test Method described herein. The second polymer may have a fusion index from about 5% to about 40%, as measured using the Fusion Index Test Method described herein, and a glass transition temperature of below 15° C., as measured using the Glass Transition Temperature Test Method described herein.

The SPIM may comprise from about 1% to about 70% of the first polymer (or a mixture of first polymers) and from about 30% to about 99% of the second polymer (or a mixture of second polymers). Alternatively, the SPIM may comprise from about 5% to about 70% of the first polymer (or a mixture of first polymers) and from about 30% to about 95% of the second polymer (or a mixture of second polymers). Alternatively, the SPIM may comprise from about 10% to about 70% of the first polymer (or a mixture of first polymers) and from about 30% to about 90% of the second polymer (or a mixture of second polymers). Alternatively, the SPIM may comprise from about 20% to about 70% of the first polymer (or a mixture of first polymers) and from about 30% to about 80% of the second polymer (or a mixture of second polymers). Alternatively, the SPIM may comprise from about 30% to about 60% of the first polymer (or a mixture of first polymers) and from about 40% to about 70% of the second polymer (or a mixture of second polymers). Alternatively, the SPIM may comprise from about 25% to about 65% of the first polymer (or a mixture of first polymers) and from about 35% to about 75% of the second polymer (or a mixture of second polymers). Alternatively, the SPIM may comprise from about 25% to about 35% of the first polymer (or a mixture of first polymers) and from about 65% to about 75% of the second polymer (or a mixture of second polymers). Alternatively, the SPIM may comprise from about 55% to about 65% of the first polymer (or a mixture of first polymers) and from about 35% to about 45% of the second polymer (or a mixture of second polymers). Alternatively, the SPIM may comprise from about 28% to about 32% of the first polymer (or a mixture of first polymers) and from about 68% to about 72% of the second polymer (or a mixture of second polymers). Alternatively, the SPIM may comprise from about 58% to about 62% of the first polymer (or a mixture of first polymers) and from about 38% to about 42% of the second polymer (or a mixture of second polymers). All percentages are by weight of the SPIM.

If a blend or mixture of more than one first polymers (of same or different class) or a blend or mixture of more than one second polymers is used, the different first polymers or second polymers may be used in equal parts by weight.

The first polymers of "class 1" may be copolymers of propylene and ethylene containing greater than 80 wt. % of polypropylene with isotactic stereochemistry, and the copolymers may be produced by using metallocene catalysts. Examples of such copolymers are commercially available as the Vistamaxx series from ExxonMobil. These copolymers may have a fusion index of about 10%, as measured using the Fusion Index Test Method described herein, and a glass transition temperature of below 0° C., as measured using the Glass Transition Temperature Test Method described herein.

Nonlimiting examples of commercially available first polymers of "class 1" are Affinity EG 8200G, Engage 8200, Infuse 9817, Vistamaxx 2330, Vistamaxx 3000, Vistamaxx 6102, Vistamaxx 6502, VERsify 4200, VERsify 4301, Vestoplast 828, and Vestoplast 703. The first polymers of "class 1" may be Vistamaxx 3000 and/or Vistamaxx 6502.

The first polymer of "class 3" may have A-B-A triblock structures, A-B diblock structures, or (A-B)n radial structures wherein the A blocks are non-elastomeric polymer blocks, typically comprising polystyrene, and the B blocks are unsaturated conjugated diene or partly hydrogenated versions of such. The B block may be selected from the group consisting of polyisoprene, polybutadiene, poly-ethylene/butane (hydrogenated polybutadiene), poly-ethylene/propylene (hydrogenated polyisoprene) and mixtures thereof. Styrenic block copolymers with hydrogenated B blocks may be used, such as poly-ethylene/butane (hydrogenated polybutadiene). A nonlimiting example of a commercially available first polymer of "class 3" is Kraton MD 1648, which has a glass transition temperature of −50° C., as measured using the Glass Transition Temperature Test Method described herein, and a fusion index of 0%, as measured using the Fusion Index Test Method described herein.

The second polymer may be a copolymer of at least two of propylene, ethylene, and/or other olefins selected from the group of higher alpha olefins with 4 to 20 carbon atoms, and the copolymer may be produced using metallocene catalysts. The second polymer may only comprise propylene and ethylene derived units and the content of ethylene derived units may be lower than 30%. Nonlimiting examples of such copolymers are commercially available as the Licocene series from Clariant. They may have a glass transition temperature below −10° C., as measured using the Glass Transition Temperature Test Method described herein. Nonlimiting examples are Licocene 1302, Licocene 1502, Licocene 1602, Licocene 2502 and Licocene 2602, available from Clariant. Licocene 1602, Licocene 2502 and/or Licocene 2602 may be used. Alternatively, Licocene 2502 may be used. Licocene 2502 has a glass transition temperature of −19° C., as measured using the Glass Transition Temperature Test Method described herein, and a fusion index of 27%%, as measured using the Fusion Index Test Method described herein.

Alternatively, polyolefinic homopolymers having propylene derived units may be used as second polymers. Such homopolymers are commercially available as the L-Modu series from Idemitsu.

The SPIM may comprise at least one component whose peak molecular weight is less than 9,000 g/mol, using the Peak Molecular Weight Test Method described herein. The SPIM may comprise at most about 50% by weight of these components with peak molecular weights less than 9,000 g/mol. The superabsorbent polymer immobilizing material may comprise at most about or less than 45%, 40%, 35%, 30%, 25%, 20%, 15%, 10%, 5%, 3%, 2%, or 1% by weight of components having a peak molecular weight less than 9,000 g/mol. These components with lower peak molecular weights may be additives, such as plasticizers, oils, waxes, surfactants, crystallinity enhancers, and/or other materials typically mixed with high peak molecular weight polymers in order to be used in hotmelt compositions for absorbent articles, as are known in the art. The SPIM may be substantially free of a tackifier. Alternatively, the SPIM may comprise at most about 15%, 10%, 5%, 3%, 2%, 1%, 0.5%, 0.1%, or about 0.01% tackifier. Alternatively, the SPIM may comprise 0% tackifier. The SPIM superabsorbent polymer immobilizing material may be substantially free of any tackifiers, waxes, oils, and plasticizers. Substantially free, as used herein, means less than 1% of a tackifier.

The SPIM may have a Storage Modulus at 25° C. of less than $1.2 \times 10^9$ Pa, as measured by the Oscillatory Rheometry Test Method described herein. The first polymer and/or the second polymers may also have a Storage Modulus at 25° C. of less than $1.2 \times 10^9$ Pa, as measured by the Oscillatory Rheometry Test Method described herein.

The SPIM may have a heat of fusion value of less than 80 J/g, alternatively less than 50 J/g, alternatively less than 40 J/g, alternatively less than 35 J/g, alternatively from about 2 J/g to about 80 J/g, alternatively from about 5 J/g to about 50 J/g, and alternatively from about 7 J/g to about 35 J/g, according to the Heat of Fusion Test Method described herein. The first polymer and the second polymer may also have a heat of fusion value of less than 80 J/g, alternatively less than 50 J/g, alternatively less than 40 J/g, alternatively less than 35 J/g, alternatively from about 2 J/g to about 80 J/g, alternatively from about 5 J/g to about 50 J/g, and alternatively from about 7 J/g to about 35 J/g, according to the Heat of Fusion Test Method described herein.

The SPIM may be soluble in organic solvents at room temperature or elevated temperature. The SPIM may comprise additives, such as some amount of tackifier, plasticizer, oil, waxes, and/or other materials as are known in the art.

Any additive may be considered if it has a peak molecular weight less than 9,000 g/mol, according to the Peak Molecular Weight Test Method described herein.

As used herein, the term "tackifying resin" or "tackifier" includes:

(a) aliphatic and cycloaliphatic petroleum hydrocarbon resins having Ring and Ball softening points of from 10° C. to 160° C., as determined by ASTM method E28-58T, the latter resins resulting from the polymerization of monomers consisting primarily of aliphatic and/or cycloaliphatic olefins and diolefins; also included are the hydrogenated aliphatic and cycloaliphatic petroleum hydrocarbon resins; examples of such commercially available resins based on a C5 olefin fraction of this type are Piccotac tackifying resin sold by Eastman Chemical Company and Escorez 131OLC sold by ExxonMobil Chemical Company;

(b) aromatic petroleum hydrocarbon resins and the hydrogenated derivatives thereof;

(c) aliphatic/aromatic petroleum derived hydrocarbon resins and the hydrogenated derivatives thereof;

(d) aromatic modified cycloaliphatic resins and the hydrogenated derivatives thereof;

(e) polyterpene resins having a softening point of from about 10° C. to about 140° C., the latter polyterpene resins generally resulting from the polymerization of terpene hydrocarbons, such as the mono-terpene known as pinene, in the presence of Friedel-Crafts catalysts at moderately low temperatures; also included are the hydrogenated polyterpene resins;

(f) copolymers and terpolymers of natural terpenes, e.g., styrene/terpene, a-methyl styrene/terpene and vinyl toluene/terpene;

(g) natural and modified rosin such as, for example, gun rosin, wood rosin, tall-oil rosin, distilled rosin, hydrogenated rosin, dimerized rosin and polymerized rosin;

(h) glycerol and pentaerythritol esters of natural and modified rosin, such as, for example, the glycerol ester of pale wood rosin, the glycerol ester of hydrogenated rosin, the glycerol ester of polymerized rosin, the pentaerythritol ester of pale wood rosin, the pentaerythritol ester of hydrogenated rosin, the pentaerythritol ester of tall-oil rosin, and the phenolic modified pentaerythritol ester of rosin; and (i) phenolic-modified terpene resins such as, for example, the resin product resulting from the condensation in an acidic medium of a terpene and a phenol.

Tackifiers can also include polar tackifying resins. Suitable resins are aliphatic petroleum hydrocarbon resins examples of which are based on C5 olefins such as Hercotac 1148 available from Hercules Corp. Also suitable are non-polar products which are hydrogenated dicyclopentadiene (DCPD) based or aromatically modified derivatives thereof with softening points above 70° C. Examples of such resins are Escorez 5400 and Escorez 5600 sold by ExxonMobil Chemical Company.

It has been found that tackifiers are typically odorous materials which give a characteristic smell to an absorbent article. To improve the consumer perception of the product, it is desired to avoid such smell by avoiding the use of tackifiers.

A plasticizer may be present in the SPIM in amounts of 0% to about 10% by weight. A suitable plasticizer may be selected from the group which includes the usual plasticizing oils, such as mineral oil, but also olefin oligomers and low molecular weight polymers, as well as vegetable and animal oils and derivatives of such oils. The petroleum derived oils which may be employed are relatively high boiling materials containing only a minor proportion aromatic hydrocarbons. In this regard, the aromatic hydrocarbons may be less than 30% or less than 15% of the oil, as measured by the fraction of aromatic carbon atoms. The oil may be essentially non-aromatic. The oligomers may be polypropylenes, polybutenes, hydrogenated polyisoprenes, hydrogenated polybutadiens, or the like having average molecular weight between about 350 and about 9,000. Suitable vegetable and animal oils include glycerol esters of the usual fatty acids and polymerization products thereof. Other useful plasticizers can be found in the families of conventional dibenzoate, phosphate, phthalate esters, as well as esters of monoorpolyglycols. Examples of such plasticizers includes, but are not limited to dipropylene glycol dibenzoate, pentaerythritoltetrabenzoate, 2-ethylhexyl diphenyl phosphate, polyethylene glycol 400-di-2-ethylhexoate; butyl benzyl phthalate, dibutyl phthalate and dioctylphthalate.

A wax may be present in the superabsorbent polymer immobilizing material in amounts from 0% to about 35%, from about 5% to about 30%, or from about 10% to about 25%, by weight of the SPIM. The wax may be any of those conventionally used in hot melt compositions. Exemplary petroleum derived synthetic waxes are paraffin and microcrystalline waxes having melting points within a range of from about 55° C. to about 110° C., as well as low molecular weight polyethylene and Fischer-Tropsch waxes.

A surfactant used may have an HLB of less than 15, the said surfactant consisting of a fatty acid ester incorporated into the composition in an amount such that the resultant composition has a contact angle of 75° or less, and alternatively less than 40°. Contact angle measurements of liquid droplets on substrate surfaces are used to characterize surface wettability. The contact angle is defined as the angle between the substrate support surface and the tangent line at the point of contact of the liquid droplet with the substrate. The value of the contact angle of the liquid droplet will depend upon the surface energy of the substrate and the surface tension of the liquid. If complete wetting takes place between the liquid and the substrate surface, the droplet will spread out over the substrate and the contact angle will approach zero, whereas if wetting is only partial, the resulting contact angle will lie in the range of about 0 degrees to about 180 degrees.

A low contact angle is desirable so that water, urine or other water-based discharges "wet out" rather than "bead up". The lower the contact angle, the more hydrophilic is the material. The water contact angle may be measured by ASTM D5946-96.

Additional examples of suitable surfactants include, but are not limited to, the following: (1) Fatty acid esters such as glycerol esters, PEG esters, and sorbitan esters, including ethylene glycol distearate, ethylene glycol monostrearate, glycerol mono and/or dioleate, PEG dioleate, PEG monolaurate, sorbitan monolaurate, sorbitan trioleate, etc. These surfactants are available from ICI, Rhone-Poulenc, and other sources; (2) Nonionic ethoxylates, such as alkylphenol ethoxylates, alcohol ethoxylates, alkylamine ethoxylates, etc., including octylphenol ethoxylate, nonylphenol ethoxylate, alkylamine ethoxylates, etc. These surfactants are available from Rhone-Poulenc, Union Carbide, and other sources; (3) Nonionic surfactants such as 2,4,7,9-tetramethyl-5-decyn-4,7-diol available from Air Products; (4) Ethylene oxide/Propylene oxide copolymers, which are available from Union Carbide, BASF, etc.; (5) Atmer 688, a nonionic surfactant blend, and Alkamuls GMS/C a glycerol monostearate, both manufactured by ICI Americas Inc. It should be noted that these and other surfactants can be blended if necessary to produce the best blend of hydrophilic performance properties. Other suitable surfactants may be found in U.S. Pat. No. 6,380,292, which is hereby incorporated by reference.

Crystallinity enhancers that may be added to the SPIM include, but are not limited to, microcrystalline waxes and crystalline olefin homopolymers. In particular, a linear polyethylene homopolymer may be used. Without being bound by theory it is believed that such materials crystallize more readily as temperature decreases due to minimal branching. The crystallites thus formed then serve as a template for crystallization of the polymeric material. In addition, crystallinity enhancers can be very small solid particles that act as a foreign phase providing a new surface on which crystal growth can occur. This foreign phase takes the form of a nucleating agent which has been designed to have a good epitaxial match with the growing polymer crystal. A uniform dispersion of these particles increases the crystallization nucleation and growth. Nucleation agents may be helpful for speeding up the transformation of the superabsorbent polymer immobilizing material from the molten state when it is applied to the superabsorbent. Examples of nucleation agents that work as crystallinity enhancers include inorganic and ceramic powders such as zirconia, calcium carbonate, magnesium silicate, silica gels, clays such as bentonite, metal oxides, and their organically modified versions thereof. Organic materials and salts can also work as nucleation agents, examples are aromatic carboxylic acid salts, sodium benzoate, and certain pigment colorants. Commercial examples of nucleation agents include the Hyperform® products from Milliken. The SPIM may comprise less than 5%, alternatively from about 1% to about 5%, alternatively from about 0.1% to about 1%, alternatively from about 0.5% to about 2%, alternatively from about 2% to about 4% of a crystallinity enhancer, by weight of the SPIM.

The SPIM may have a Shear Viscosity at 10 (1/s) at 230° C. of from about 300 mPa·s to about 10,000 mPa·s, alternatively from about 750 mPa·s to about 9,750 mPa·s, alternatively from about 1,000 mPa·s to about 9,500 mPa·s, alternatively from about 2,000 mPa·s to about 9,250 mPa·s, alternatively from about 3,000 mPa·s to about 9,000 mPa·s, alternatively from about 4,000 mPa·s to about 8,750 mPa·s, alternatively from about 4,750 mPa·s to about 8,500 mPa·s, alternatively from about 5,100 mPa·s to about 8,250 mPa·s, alternatively from about 5,000 mPa·s to about 5,500 mPa·s, and alternatively from about 7,900 mPa·s to about 8,400 mPa·s, according to the Viscosity Rheometry Test Method described herein.

The SPIM may have a Wet Mobilization Value of less than 50%, alternatively less than 40%, alternatively less than 30%, alternatively from about 0% to about 50%, alternatively from about 5% to about 45%, and alternatively from about 10% to about 28%, according to the Wet Mobilization Value Test Method described herein.

The SPIM may have a Storage Modulus at 100° C. of from about 200 Pa to about 400,000 Pa, alternatively from about 300 Pa to about 300,000 Pa, alternatively from about 400 Pa to about 200,000 Pa, alternatively from about 500 Pa to about 150,000 Pa, alternatively from about 600 Pa to about 100,000 Pa, alternatively from about 700 Pa to about 95,000 Pa, alternatively from about 650 Pa to about 800 Pa, and alternatively from about 90,000 Pa to about 92,000 Pa, according to the Oscillatory Rheometry Test Method described herein.

The SPIM may have a Loss Factor at 100° C. of from less than 10, alternatively less than 8, alternatively less than 6, and alternatively less than 5, according to the Oscillatory Rheometry Test Method described herein.

The SPIM may have a Strain Hardening Index of from about 25 to about 1,000, alternatively from about 30 to about 500, alternatively from about 35 to about 125, alternatively from about 35 to about 100, and alternatively from about 35 to about 75, according to the Extensional Test Method described herein.

The SPIM may have a Strain at Break of at least 2.2, alternatively from about 2.2 to about 8.5, according to the Extensional Test Method described herein.

EXAMPLES

The following examples are given solely for the purpose of illustration, and are not to be construed as limitations since many variations thereof are possible without departing from the scope of the absorbent article described herein.

TABLE 1

| | Licocene 2502[1] | Vistamaxx 6502[2] | Kraton MD 1648[3] |
|---|---|---|---|
| Example 1 | 70% | 30% | |
| Example 2 | 40% | | 60% |
| Comparative Example 1 | 100% | | |
| Comparative Example 2 | | 100% | |
| Comparative Example 3 | | | 100% |

[1]Available from Clariant
[2]Available from ExxonMobil
[3]Available from Kraton Polymers LLC DATA

TABLE 2

| | Peak Molecular Weight [g/mol] | Viscosity at 230° C. [mPa · s] | Wet Mobilization Value [%] | Storage Modulus at 100° C. [Pa] | Loss Factor at 100° C. | Strain Hardening Index |
|---|---|---|---|---|---|---|
| Example 1 | NA | 5,256 | 25 | 719 | 4.01 | 71 |
| Example 2 | NA | 8,140 | 12 | 90,831 | 0.48 | 39 |
| Comparative Example 1 | 57,100 | 163 | 100 | 7 | 58.9 | 19 |
| Comparative Example 2 | 185,300 | 119,478 | (clogged equipment) | 24,594 | 1.54 | 458 |
| Comparative Example 3 | 104,000 | 37,463 | (clogged equipment) | 468,055 | 0.38 | 208 |

For Comparative Example 2 and Comparative Example 3, it was not possible to make core bags for subjection to the Wet Mobilization Value Test Method because the equipment was clogged up due to the viscosity.

The inventors have found that a sufficiently high molecular weight of at least one ingredient of the SPIM is required to enable a sufficient strength of the polymers in the molten state that is pertinent for processing.

With regards to the Wet Mobilization Value, in all three cases fibrous nets of fibers were formed with a fiber diameter of about 10 μm to about 15 μm and hole sizes of the net of from about 400 μm to about 500 μm. There was, however, one salient difference: the fibers of nets generated with Example 1 and Example 2 had a rather round shape (i.e. a rather circular cross-section) and they spanned over the interstitials between the SAP particles, onto which they had been sprayed. The fibers of the nets generated with Comparative Example 1 were rather flat in shape and did not span over the interstitials between the SAP particles; on the contrary, they completely conformed to the interstitials between the SAP particles. Furthermore, the fibrous nets formed with Example 1 and Example 2 appeared rather coherent and intact, while the nets formed with Comparative Example 1 appeared rather fragmented and partially torn on visual inspection.

The interstitials between the SAP particles have height of from about 300 μm to about 800 μm. The inventors believe that a net consisting of flat fibers which conforms to the "hill and valley structure" of the SAP particle layer has a weaker mechanical strength than a net consisting of round fibers which bridges the interstitials.

The visual inspection was carried out via Scanning Electron Microscopy and via Light Microscopy. To facilitate the visual inspection via light microscopy, a blue pigment had been added in a very small concentration to all formulations tested.

The inventors believe that a fibrous net with rather round and non-conforming fibers leads in general to a better mechanical stabilization, and is in general better able to withstand forces. This can be seen from the superior performance of Example 1 and Example 2.

To measure the Wet Mobilization Value, core bags (absorbent cores) were made with the different SPIMs (Superabsorbent Polymer Immobilizer Materials) from Table 1. Example 1, Example 2 and Comparative Example 1 and were subjected to the Wet Mobilization Value Test Method described herein.

The core bags used to measure the Wet Mobilization Value data in the following Table 2 were made by applying the method disclosed for making absorbent layers disclosed in WO2008/155699, which is hereby incorporated by reference, with some adaptations. The method is schematically disclosed in FIG. 15.

Figure 15:
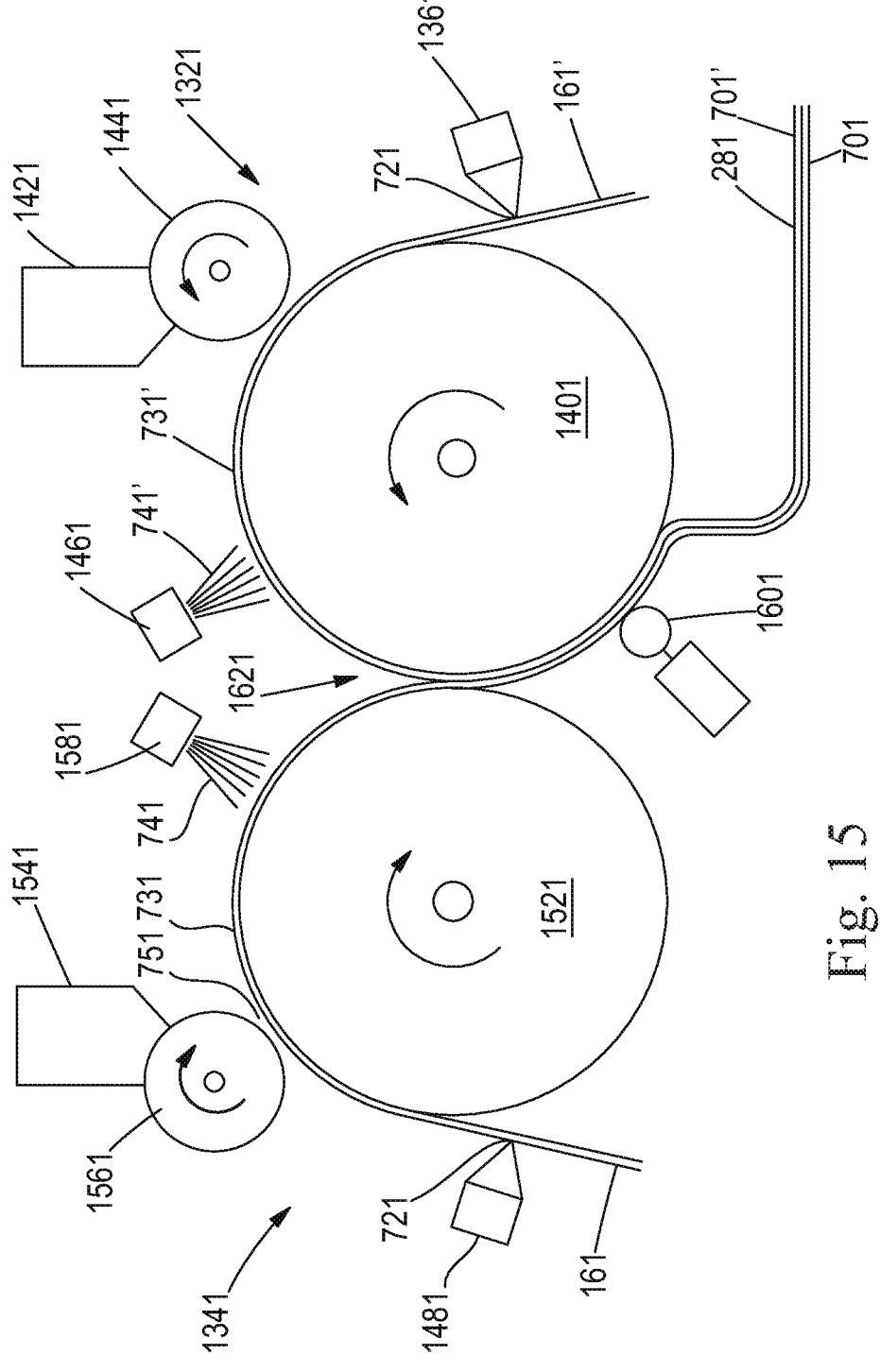
FIG. 15 is an additional schematic illustration of an exemplary process for making an absorbent core in accordance with the absorbent article described herein.

A first printing unit 1341 for making an absorbent structure is illustrated on the left side of FIG. 15. The first printing unit 1341 comprises an auxiliary glue applicator 1481 for applying the auxiliary glue 721 to the substrate 161, a first rotatable support roll 1521 for receiving the first substrate 161 ("dusting layer nonwoven"), a first hopper 1541 for holding and dispensing the superabsorbent particulate polymer material, a first printing roll 1561 for depositing the superabsorbent particulate polymer material (i.e. the SAP) land areas 751 from the hopper 1541 to a deposition area 731 on the substrate 161, and a first thermoplastic polymer material (i.e. SI) applicator 1581 for applying the fibrous thermoplastic polymer material 741. The auxiliary glue applicator 1481 may be a nozzle system which can provide a relatively thin but wide curtain of thermoplastic adhesive material as suggested in WO2008/155699, which is hereby incorporated by reference, but may also alternatively and advantageously comprise a slot coater for applying simultaneously several slots of auxiliary glue 721 longitudinally along the width of the substrate. The auxiliary glue applicator may be fitted with a manifold which intermittently stops the delivery of the auxiliary glue so that there the auxiliary layer is not applied or applied at a reduced amount in the area of the substrate corresponding to the zones of lower absorbent material amount. The SAP printing roll 1561 and fibrous layer adhesive applicator 1581 may be as further detailed in WO2008/155699, which is hereby incorporated by reference.

The absorbent structure 701 obtained by the printing unit 1341 is combined with a second absorbent structure 701', to form an absorbent core. This second absorbent structure 701' is formed on the second printing unit 1321 as shown on the right side of FIG. 15, which may be generally identical to the first printing unit 1341. The second printing unit 1321 comprises a second auxiliary glue applicator 1361 which may be a slot coater for applying an auxiliary glue to the second substrate 161' ("core cover nonwoven"), a second rotatable support roll 1401 for receiving the substrate 161', a second hopper 1421 for holding superabsorbent particulate polymer material, a second printing roll 1441 for transferring the superabsorbent particulate polymer material to the substrate 161', and a thermoplastic adhesive material applicator 146 for applying the thermoplastic fibrous adhesive material 741' to the substrate 161' and the superabsorbent particulate polymer land areas 751' thereon.

The absorbent structures are combined by applying pressure in the nip between the two support rolls 1401, 1521. The longitudinal side seals 2841, 2861 may be formed for example as a C-wrap in the seal forming guide roller 1601. The absorbent cores 281 can then be individualized by forming the front and back end seals and cutting the web of the core material at the required interval.

For Example 1, Example 2 and Comparative Example 1, the SPIM was applied with a basis weight of 3 g/m² via each of the two thermoplastic adhesive material applicators 1581 and 1461. The application temperature for the SPIM was 230° C. The superabsorbent polymer material was applied in a basis weight of 1381 g/m² via each of the two printing rolls 1561 and 1441. For Example 1, Example 2 and Comparative Example 1, the superabsorbent polymer material particles were deposited onto a total area of 340 mm (machine direction)×110 mm (cross direction) per core bag. The auxiliary glue was only applied onto the second substrate 161', i.e. not onto the first substrate 161, via a slot application and with a basis weight of 8 gsm. As auxiliary glue any hot melt adhesive materials described in U.S. 2014/0358100 can be used, which is hereby incorporated by reference; for the present examples DM 3800 from Henkel was used.

As first substrate ("dusting layer nonwoven") an SMS nonwoven with a basis weight of 10 gsm, as the second substrate ("core cover nonwoven") an SMS nonwoven with a basis weight of 8 gsm was used.

Test Methods

Peak Molecular Weight Test Method

Molecular weight, as used herein, refers to peak molecular weight, as determined using a gel permeation chromatography (GPC) method. GPC is a well-known method wherein polymers are separated according to molecular size, the largest molecule eluting first. The chromatograph is calibrated using commercially available polystyrene molecular weight standards. The peak molecular weights referred to herein can be determined with gel permeation chromatography (GPC) using polystyrene calibration standards, such as is done according to ASTM D5296. The molecular weight of any polymer or unknown polymer measured using GPC so calibrated is the styrene equivalent molecular weight, which herein is defined as the "peak molecular weight." Suitable solvents and temperatures are employed with GPC in order to achieve adequate molecular weight separation and resolution.

Viscosity Rheometry Test Method

The Viscosity Rheometry Test Method is used to measure the shear viscosity at a shear rate of 10 [1/s] at 230° C. of a polymer composition.

A controlled-strain rotational rheometer (such a ARES G2, TA Instruments, New Castle, DE, USA, or equivalent) capable of sample temperature control (such as a Forced Convection Oven; TA Instruments, New Castle, DE, USA, or equivalent)) with a precision equal to or exceeding +/−0.5° C. at 230° C. is used. The rheometer is operated in a cone-to-plate configuration, with 25 mm 0.1 rad steel cone as upper tool and a 40 mm steel plate lower tool. The cone truncation distance is defined as that specified for the particular cone tooling used (typically approximately 50 μm for a 25 mm 0.1 rad steel cone). The cone truncation distance is controlled to the nearest 0.1 μm.

The rheometer is heated to 190° C. and polymer composition is introduced in the rheometer. Once the polymer has equilibrated in temperature at 190° C., the rheometer tooling gap is set to 50 μm greater than the cone truncation distance and excess protruding sample is trimmed. The gap is then set to the cone truncation distance. To condition the sample a constant pre-shear of 0.1 1/s, at 190° C. for 180 s is applied.

For the measurement the rheometer temperature is set to 230° C. and when sample has reached temperature it is conditioned for 180 s. A steady state shear rate of 10 1/s is applied. The viscosity is measured with a sampling period of 15 sec. The viscosity is calculated and the average of each period is monitored. When three viscosity periods in a row are within +/−5% of each other, the average (arithmetic mean) of these three values is reported as steady state viscosity at 10 1/s and 230° C. and this value is reported in millipascal seconds (mPa·s) to the nearest 1 (mPa·s) as the "Shear Viscosity at 10 (1/s) at 230° C.".

Wet Mobilization Value Test Method

Equipment

Graduated Cylinder

Stop watch (±0.1 sec)

Scissors

Light Box

Pen

Test solution: 0.90% saline solution at 23+/−2° C.

Metal ruler traceable to NIST, DIN, JIS or other comparable National Standard

PVC/metal dishes with a flat surface inside and a minimum length of the core bag length (n) to be measured and a maximum length n+50 mm, width w±50 mm, height of 30-100 mm or equivalent

36

Balance accurate to ±0.0.1 g

Binder clips width 1" (25 mm)

Wet Immobilization Impact Tester Equipment (WAIIT-3), Design package number: PA-00112.59506-R03, Manufacturing information: Henkel GmbH Germany The WAIIT tester is a purely mechanical device. A sliding-board (A) is falling down along a sliding track (B) after it was mechanical released by two levers placed on the side of the equipment. A pre-loaded diaper is cut (cross direction) and is attached onto the sliding-board with the open side down. The sliding-board is lifted up by the operator using his hands. After releasing the sliding-board, it hits the anvil below and the impact force damages the absorbent core structure. Depending on the absorbent core structure quality AGM particles will fall out of the pad. The weight difference before and after the impact describes the quality of the absorbent core.

Facilities:

Standard laboratory conditions, temperature: 23° C.±2° C., relative humidity: <55%

Sample Preparation:

1. Open the product, topsheet side up.
2. Unfold the diaper and cut the cuff elastics approximately every 2.5 cm to relieve chassis tension such that the product easily lies flat.
3. For pull-up products open the side seams and remove the waistbands.
4. Remove the topsheet and potential other layers or materials between topsheet and core bag so as to minimally perturb the core bag nonwovens and absorbent material contained within. Note: steps 1 to 4 are not required if the core bags have been directly made, as in the examples, and do not need to be separated from diapers.
5. A lightbox is used to identify the longitudinal extent of the core, and the longitudinal midpoint of the core along the longitudinal axis is marked.

Test Procedure

WAIIT Calibration

1. Make sure that the sliding board is in the lower position. Open the front door of the WAIIT tester and connect the force gauge hook to the upper sample clamp of the WAIIT. Make sure that the clamp is closed before connecting the spring-balance.
2. Use both hands on the spring-balance to lift continuously and as slowly as possible up the sliding board towards the upper position. Record the average value ($m_1$) during the execution to the nearest 0.02 kg.
3. Guide down the sliding board as slowly as possible to the lower position and record the average value ($m_2$) read off during execution to the nearest 0.02 kg.
4. Calculate and record the delta of $m_1-m_2$ to the nearest 0.02 kg. If the delta is 0.6 kg±0.3 kg continue measurement. Otherwise, an adjustment of the sliding board is necessary. Make sure that the sliding board is in lower position and check the sliding path for any contamination or damage. Check if the position of the sliding board to the sliding path is correctly adjusted by shaking the board. For easy gliding some clearance is needed. If not present, readjust the system.

WAIIT Test Settings

Drop height is 16 cm.

Core capacity (cc) is calculated as: $cc=m_{SAP}\times SAP_{GV}$, where $m_{SAP}$ is the mass of superabsorbent polymer (SAP) present in the diaper and $SAP_{GV}$ is the free swelling capacity of the superabsorbent polymer. Free swelling capacity of the superabsorbent polymer is determined with the method described in WO 2006/062258, which is hereby incorporated by reference. The mass of the superabsorbent polymer present in the diaper is the average mass present in ten products.

Test Execution

1. Weigh and report it to the nearest 0.1 g.
2. Measure the appropriate volume Saline (0.9% NaC1 in deionized water) with the graduated cylinder.
3. Lay the dish flat on the laboratory table. Lay the core bag, topsheet side down, flat into the filled plastic or metal dish. Wait for 5±1 min to allow all saline to be absorbed. After this period, there might be liquid in the dish at the sides of the core which has not been in contact with the core. If this is the case, take the dish and hold it slanting in different directions, to allow any free liquid to be absorbed.
4. Wait for another 5 minutes (+/–30 sec) to allow all saline to be absorbed. Some drops may be retained in the dish. Use only the defined PVC/metal dish to guarantee homogenous liquid distribution and less retained liquid
5. Weigh and report it to the nearest 0.1 g. Check to see if the wet core bag weight is out of limit (defined as "dry core bag weight+diaper load±4 ml"). For example, 12 g dry core bag weight+150 ml load=162 g wet core bag weight. If the actual wet weight on the scale is between 158 g and 166 g, the pad can be used for shaking. Otherwise discard the pad and repeat all steps.
6. The loaded core bag is cut parallel to the lateral axis and through the longitudinal midpoint of the core so as to divide the core bag into approximately two "halves"— one corresponding to the front of the absorbent article and one corresponding to the rear of the absorbent article.
7. Weigh the back of the cut wet core bag and record it to the nearest 0.1 g.
8. Take the back of the cut wet core bag and clamp the end seal side up into the WAIIT (open end of the core oriented down). Thereby, the back of the cut wet core bag is folded around the top edge of the sliding board and fixed with two binder clips (width=25 mm) onto the sliding board. The core bags are clamped in a way that the clamps overlap with the AGM containing area of the core over a length of 1 cm in vertical direction. Press the pad onto the sliding board to establish a connection. Note: Make sure that enough diaper material is folded around the top edge of the sliding board so that the clamps do not touch the sliding board material. This is needed to have a proper fixation of the sample during impact. It is allowed to clamp the absorbent core.
9. Lift up the sliding board to the upper position by using both hands until the board is engaged.
10. Close the safety front door and release the slide blade using both levers on the side simultaneously.
11. Take the tested sample out of the WAIIT and put it on the balance ($m_2$). Record the weight to the nearest 0.1 g.
12. Repeat steps 5 to 13 with front of the cut wet core bag.
Reporting:
1. Record the dry core bag weight to the nearest 0.1 g.
2. Record the wet weight before ($m_{1front}$ and $m_{1back}$) and after ($m_{2front}$ and $m_{2back}$) testing, both to the nearest 0.1 g.

3. Calculate and report the average weight loss ($\Delta m$) to the nearest 0.1 g: $\Delta m=(m_{1front}+m_{1back})-(m_{2front}+m_{2back})$
4. Calculate and report the weight loss in percent to the nearest 1%, ($\Delta m_{rel}$): $(\Delta m_{rel})=(((m_{1front}+m_{1back})-(m_{2front}+m_{2back}))\times100\%)/(m_{1front}+m_{1back})$ In total, ten replicates are performed. For each replicate the percent weight loss is calculated and recorded. The arithmetic mean of percent weight loss for the ten replicates is calculated and reported in percent, to the nearest integer value of percent, as the Wet Mobilization Value.

Oscillatory Rheometry Test Method

The Oscillatory Rheometry Test Method is used to measure the Storage Modulus and the Loss Factor of a polymer composition. A controlled-strain rotational rheometer (such as Discovery HR-3, TA Instruments, New Castle, DE, USA, or equivalent) capable of sample temperature control (using a Peltier cooler and resistance heater combination) with a precision equal to or exceeding 0.5° C. over at least the range of –10° C. to 150° C. The rheometer is operated in a parallel plate configuration with 20-mm stainless steel parallel-plate tooling.

A parallel plate gap of 1000 μm is initially used in the method. To compensate for thermal expansion of the tooling, the gap is set to 1000 μm, and a mapping of actual plate gap (as measured using a suitable standard test fluid) a function of temperature over the range –10° C. to 150° C. is performed. This mapping is then used throughout the determination of the Storage Modulus Parameter and the Loss Factor Parameter.

The rheometer is heated to 150° C., the polymer composition is introduced in the rheometer, the gap is set to 1050 μm, excess protruding sample is trimmed, and the gap is then set to 1000 μm. (The axial force control of the rheometer is set to 0 N and be maintained within ±0.1 N of force during the experiment, thereby thermal expansion/contraction of the sample itself is compensated by adjusting the gap in order to avoid overfilling or underfilling in addition to the abovementioned compensation of the tooling.) The rheometer is then allowed to cool to 130° C., at which point the measurement commences with temperature ramped from 130° C. to –10° C. at a constant rate of cooling of 2° C./min. The applied strain amplitude is 0.1%, and the frequency of oscillation is 1 Hz (that is, one cycle per second). The resulting oscillatory stress is recorded.

After this step, the sample temperature is set to 23° C. (temperature is ramped to this setpoint at a rate of 10° C./min), and the sample is allowed to rest for 4.0 hours at 23° C. At the end of this period, the temperature is set to –10° C. (temperature is ramped to this setpoint at a rate of 10° C./min), the sample is equilibrated for 300 seconds at –10° C., and a second oscillatory rheology measurement is conducted (0.1% strain, frequency of oscillation of 1 Hz) while temperature is ramped upward to 130° C. at a constant rate of increase of 2° C./min.

From the first decreasing temperature sweep, the storage modulus G' is calculated and recorded at 100° C., and these values are reported in Pascals (Pa) to the nearest 1 Pa as the "Storage Modulus at 100° C.". From the first, decreasing temperature sweep, the loss factor (also known as tan delta) is calculated recorded at 100° C., and this dimensionless value is reported to the nearest hundredth as the "Loss Factor at 100° C.".

The storage modulus G' can also be calculated and recorded at different temperatures, such as 25° C.

Extensional Test Method

The Extensional Test Method is used to determine the Yield Stress Parameter, the Max Stress Parameter, the Strain to Break Parameter, and the Strain Hardening Index for a specimen of a polymer composition. A thin film specimen formed of polymer composition is analyzed with a rotational rheometer fitted with a specialized fixture with counter rotating rollers, and the stress associated with extensional strain imparted is measured and recorded.

Instrumental Setup

A rotational rheometer (ARES G2, TA Instruments, New Castle, DE, USA, or equivalent) is fitted with a fixture that has counter rotating cylindrical rollers specifically designed for the interrogation of extension deformation of films. An example of a suitable fixture is the Extensional Viscosity Fixture, or EVF (EVF, TA Instruments, or equivalent). The rheometer is further fitted with a forced-convection oven FCO (FCO, TA Instruments, or equivalent) and cooling system (ACS 2, TA Instruments, or equivalent) capable of controlling temperate from at least −50 to 250° C. to a within a tolerance of 0.5° C.

Specimen Preparation

Approximately 10 g of the polymer composition is placed in a polytetrafluoroethane (PTFE) bowl and introduced into a vacuum oven. After 15 minutes at 170° C. at ambient pressure, the pressure is lowered to 10 mbar, and the polymer composition is subsequently held at 170° C. and at 10 mbar for 45 minutes to remove air bubbles from the polymer composition. The polymer composition is removed from the vacuum oven and allowed to cool to ambient lab conditions (23±2° C.) for 90±30 minutes, at which point the polymer composition is removed from the PTFE bowl and placed between 2 sheets of siliconized paper. A metal shim 0.50 mm in thickness is used in the heated press as a spacer to obtain a film thickness of 0.50 mm when pressed with a heated press at 90° C. and 10 Bar (instrument setting) for 60 seconds to a polymeric film. If 90° C. is insufficient to melt the polymer composition, a higher temperature (but the lowest temperature sufficient to melt the composition) is used. The film is stored at least 120 hours in the laboratory at 23±2° C. prior to testing. From the film individual specimens for measurement are punched with a sample cutter to the specimen dimensions of 20.0 mm by 10.0 mm by 0.50 mm. This specimen will be cut lengthways with a scissor to achieve a final width of 5±0.5 mm. The exact width and thickness will be determined with a digital caliper (Electronic Caliper PRO-MAX Fowler) to the nearest of 0.01 mm and entered into the rheometer software.

Measurement

The cylinders of the EVF are heated to 80° C. for 90±30 s in the forced-convection oven of the rheometer. Then a small droplet (0.03±0.01 g) of a molten hot melt adhesive is applied to each cylinder. The used adhesive should exhibit a high stiffness (G' at 23° C. greater than 10 MPa) to not interfere with the measurement. A specimen of polymer composition is quickly pressed into the molten adhesive on the cylinders of the EVF to fix it to the cylinder surface. The specimen is placed perpendicular to the axis of rotation of the cylinders.

The specimen mounted on the EVF is then placed in the forced convection oven of the rheometer for thermal conditioning and is kept isothermal at 23±1° C. for 300±10 s. After this time has elapsed, the specimen is mechanically conditioned. To mechanically condition the specimen, the torque transducer is zeroed, and the sample is put under a pre-stretch rate of 0.001 s$^{-1}$ for 0.30 s and then allowed to relax for 60 s. (In this method, all strain is expressed in terms of Hencky strain, also known as "true strain" or "logarithmic strain.")

The measurement is performed in the FCO oven at 23° C.±0.5° C. The strain rate extension for the measurement is 0.01 s-1, and the strain at maximum extension is 4.0. After measurement, the specimen is checked for rupturing. If it has ruptured, the location of the break is noted. If the rupture is approximately in the middle between the two cylinders of the EVF, the data collected are deemed acceptable. Otherwise, if the polymeric film break is at or close to the rotating cylinders, the results are discarded and the measurement performed again on a replicate specimen.

Analysis

For the extensional stress calculation, a constant volume is assumed. From the raw torque versus angular displacement data recorded by the rheometer, extensional stress (in megapascals, or MPa) versus Hencky strain data are calculated. The data are plotted in semi-logarithmic fashion with Hencky strain on the abscissa (linear scale) and extensional stress on the ordinate (logarithmic scale). A linear fit with a positive slope with an $R^2$ value of 0.9 or greater is set between a Hencky strain of 0.5 and 1. Otherwise, the maximum value of extensional stress recorded during the measurement is reported as the Yield Stress Parameter, again reported in MPa to the nearest kilopascal. The value of the fitted line at a Hencky strain of zero (that is, the y-intercept), is defined as the Yield Stress Parameter, which is reported in MPa to the nearest kilopascal. The maximum stress value in the plot is defined as the Maximum Stress Parameter, which is reported in MPa to the nearest kilopascal. The Hencky Strain, when the specimen ruptures and/or the reported torque value is lower than 100 μNm, is reported as Strain to Break Parameter as dimensionless value to the nearest of 0.1 (or, in the case it did not rupture during the measurement, to a strain of 4.0). The difference of the Maximum Stress and the Yield Stress divided by the Yield Stress is defined as Strain Hardening Index, which is reported as dimensionless value to the nearest of 1.

Enthalpy of Fusion Measurement Method

The Enthalpy of Fusion of a superabsorbent polymer immobilizing material composition is determined using the Enthalpy of Fusion Test Method, which consists of performing ASTM D3418-15 with the following additional guidance. Specimen(s) are preferably extracted from molded or pelleted raw superabsorbent polymer immobilizing material. If raw material is not available, specimen(s) of superabsorbent polymer immobilizing material are extracted from bonds of interest in an absorbent article using techniques known to those of skill in the art. Dry nitrogen is used as the purge gas in the differential scanning calorimeter (DSC). The rate of increase of temperature in the DSC is 10° C./min, and the rate of decrease of temperature in the DSC is 1° C./min. The mass-normalized enthalpy of fusion is calculated as specified in section 11.4 based on the curve corresponding to decreasing temperature (at 1° C./min) and is reported as the "Enthalpy of Fusion" in units of joules per gram (J/g) to the nearest 0.1 J/g.

Glass Transition Temperature Test Method

The glass transition temperature is determined by the measurement specified by ASTM D3418-08 "Standard Test Method for Transition Temperatures and Enthalpies of Fusion and Crystallization of Polymers by Differential Scanning calorimetry."

Heat of Fusion Test Method

Heat of fusion, as used herein, is determined using ASTM D3418-08.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:

an absorbent core comprising a superabsorbent polymer material and an auxiliary adhesive;

wherein the auxiliary adhesive comprises from about 20% to about 70% of a first polymer, by weight of the auxiliary adhesive;

wherein the auxiliary adhesive comprises from about 30% to about 80% of a second polymer, by weight of the auxiliary adhesive;

wherein the first polymer has a peak molecular weight of from about 65,000 g/mol to about 700,000 g/mol, according to the Peak Molecular Weight Test Method described herein;

wherein the first polymer is a random and/or block copolymer having ethylene derived units and/or C3-C10 alpha olefin derived units, or the first polymer is a polyolefinic homopolymer having ethylene derived units or propylene derived units or 1-butene derived units, or the first polymer is a styrenic block copolymer;

42 wherein the second polymer has a peak molecular weight of from about 1,000 g/mol to about 60,000 g/mol, according to the Peak Molecular Weight Test Method described herein;

wherein the second polymer is a polyolefin;

wherein the auxiliary adhesive has a Shear Viscosity at 10 (1/s) at 230° C. of from about 300 mPa·s to about 10,000 mPa·s, according to the Viscosity Rheometry Test Method described herein; and wherein the auxiliary adhesive is substantially free of a tackifier.

2. The absorbent article according to claim 1, wherein the peak molecular weight of the second polymer is from about 15,000 g/mol to about 60,000 g/mol.

3. The absorbent article according to claim 1, wherein the absorbent core further comprises a superabsorbent polymer immobilizing material, wherein the superabsorbent polymer immobilizing material is a fiberized net structure.

4. The absorbent article according to claim 1, wherein the absorbent article further comprises a topsheet and a backsheet, with the absorbent core disposed therebetween.

5. The absorbent article according to claim 1, wherein the absorbent core comprises a first absorbent layer comprising a first substrate, wherein at least a portion of the auxiliary adhesive is deposited on the first substrate, and wherein the first substrate is a nonwoven core cover.

6. The absorbent article according to claim 1, wherein the auxiliary adhesive has a Wet Mobilization Value of less than 50%, according to the Wet Mobilization Test Method described herein.

7. The absorbent article according to claim 1, wherein the auxiliary adhesive has a Storage Modulus at 100° C. of from about 200 Pa to about 400,000 Pa, according to the Oscillatory Rheometry Test Method described herein.

8. The absorbent article according to claim 1, wherein the auxiliary adhesive has a Loss Factor at 100° C. of less than 5, according to the Oscillatory Rheometry Test Method described herein.

9. The absorbent article according to claim 1, wherein the auxiliary adhesive has a Strain Hardening Index of from about 25 to about 1,000, according to the Extensional Test Method described herein.

10. The absorbent article according to claim 1, wherein the peak molecular weight of the first polymer is from about 75,000 g/mol to about 500,000 g/mol when the first polymer is the random and/or block copolymer having ethylene derived units and/or C3-C10 alpha olefin derived units.

11. The absorbent article according to claim 1, wherein the peak molecular weight of the first polymer is from about 65,000 g/mol to about 150,000 g/mol when the first polymer is the styrenic block copolymer.

12. An absorbent article comprising:

an absorbent core comprising a superabsorbent polymer material and an auxiliary adhesive;

wherein the auxiliary adhesive comprises from about 20% to about 70% of a first polymer, by weight of the auxiliary adhesive;

wherein the auxiliary adhesive comprises from about 30% to about 80% of a second polymer, by weight of the auxiliary adhesive;

wherein the auxiliary adhesive has a Wet Mobilization Value of less than 50%, according to the Wet Mobilization Test Method described herein;

wherein the auxiliary adhesive has a Storage Modulus at 100° C. of from about 200 Pa to about 400,000 Pa, according to the Oscillatory Rheometry Test Method described herein;

wherein the auxiliary adhesive has a Strain Hardening Index of from about 25 to about 1,000, according to the Extensional Test Method described herein; and wherein the auxiliary adhesive has a Shear Viscosity at 10 (1/s) at 230° C. of from about 300 mPa·s to about 10,000 mPa·s, according to the Viscosity Rheometry Test Method described herein.

13. The absorbent article according to claim 12, wherein the auxiliary adhesive has a Strain at Break of from about 2.2 to about 8.5, according to the Extensional Test Method described herein.

14. The absorbent article according to claim 12, wherein the first polymer has a peak molecular weight of from about 65,000 g/mol to about 700,000 g/mol, according to the Peak Molecular Weight Test Method described herein, and wherein the first polymer is a random and/or block copolymer having ethylene derived units and/or C3-C10 alpha olefin derived units, or the first polymer is a polyolefinic homopolymer having ethylene derived units or propylene derived units or 1-butene derived units, or the first polymer is a styrenic block copolymer.

15. The absorbent article according to claim 12, wherein the second polymer has a peak molecular weight of from about 1,000 g/mol to about 60,000 g/mol, according to the Peak Molecular Weight Test Method described herein, and wherein the second polymer is a polyolefin.

16. The absorbent article according to claim 12, wherein the auxiliary adhesive is substantially free of a tackifier.

17. An absorbent article comprising:

an absorbent core comprising a superabsorbent polymer material and an auxiliary adhesive;

wherein the auxiliary adhesive comprises from about 20% to about 70% of a first polymer, by weight of the auxiliary adhesive;

wherein the auxiliary adhesive comprises from about 30% to about 80% of a second polymer, by weight of the auxiliary adhesive;

wherein the first polymer has a peak molecular weight of from about 20,000 g/mol to about 700,000 g/mol, according to the Peak Molecular Weight Test Method described herein;

wherein the first polymer is a random and/or block copolymer having ethylene derived units and/or C3-C10 alpha olefin derived units, or the first polymer is a polyolefinic homopolymer having ethylene derived units or propylene derived units or 1-butene derived units, or the first polymer is a styrenic block copolymer;

wherein the second polymer has a peak molecular weight of from about 1,000 g/mol to about 90,000 g/mol, according to the Peak Molecular Weight Test Method described herein;

wherein the first polymer is different than the second polymer;

wherein the auxiliary adhesive has a Shear Viscosity at 10 (1/s) at 230° C. of from about 300 mPa·s to about 10,000 mPa·s, according to the Viscosity Rheometry Test Method described herein;

wherein the auxiliary adhesive has a Strain Hardening Index of from about 25 to about 1,000, according to the Extensional Test Method described herein; and wherein the auxiliary adhesive is substantially free of a tackifier.

18. The absorbent article according to claim 17, wherein the Strain Hardening Index is from about 25 to about 175.

19. The absorbent article according to claim 17, wherein the second polymer is a polyolefin.

20. The absorbent article according to claim 17, wherein the absorbent core has channels, and wherein the channels are free of any absorbent material.

* * * * *